(12) United States Patent
Rampersad

(10) Patent No.: US 9,033,383 B2
(45) Date of Patent: May 19, 2015

(54) DISPOSABLE FINGER TONGS FOR HANDLING A FOOD PRODUCT

(71) Applicant: Kenrick Rampersad, Brentwood, NY (US)

(72) Inventor: Kenrick Rampersad, Brentwood, NY (US)

(*) Notice: Subject to any disclaimer, the term of this patent is extended or adjusted under 35 U.S.C. 154(b) by 0 days.

(21) Appl. No.: 13/939,070

(22) Filed: Jul. 10, 2013

(65) Prior Publication Data

US 2014/0028039 A1    Jan. 30, 2014

Related U.S. Application Data

(60) Provisional application No. 61/741,052, filed on Jul. 11, 2012, provisional application No. 61/741,657, filed on Jul. 25, 2012, provisional application No. 61/796,556, filed on Nov. 13, 2012, provisional application No. 61/848,579, filed on Jan. 7, 2013.

(51) Int. Cl.
| | |
|---|---|
| *B25B 9/02* | (2006.01) |
| *A47G 21/10* | (2006.01) |
| *A61F 13/10* | (2006.01) |
| *A47J 43/28* | (2006.01) |

(52) U.S. Cl.
CPC .............. *A47G 21/10* (2013.01); *A61F 13/105* (2013.01); *A47J 43/283* (2013.01)

(58) Field of Classification Search
CPC ..... A61F 13/104; A61F 13/105; A47G 21/10; A47G 43/283
USPC ........... 294/1.3, 16, 25, 55.5, 99.1–99.2, 106, 294/176, 902; 2/17, 20–21, 160–163
See application file for complete search history.

(56) References Cited

U.S. PATENT DOCUMENTS

| | | | | |
|---|---|---|---|---|
| 567,087 | A * | 9/1896 | Fitzgeral et al. | 294/11 |
| 2,244,072 | A * | 6/1941 | Ledbetter | 294/25 |
| 3,331,626 | A | 7/1967 | Kaufman | |
| 3,407,927 | A | 10/1968 | Jones | |
| 4,038,787 | A * | 8/1977 | Bianchi | 451/523 |
| 4,188,055 | A * | 2/1980 | Green | 294/1.3 |
| 4,424,595 | A * | 1/1984 | Albert | 2/18 |
| 4,938,515 | A | 7/1990 | Fazio | |
| 5,359,840 | A * | 11/1994 | Costar | 56/400.12 |
| 5,848,928 | A | 12/1998 | Wong | |
| 6,243,868 | B1 * | 6/2001 | Wanzenried | 2/21 |
| 7,117,536 | B2 * | 10/2006 | Burnett et al. | 2/16 |
| 7,165,270 | B2 * | 1/2007 | DeYoung et al. | 2/16 |
| 8,261,938 | B2 | 9/2012 | Oradini | |
| 2005/0138736 | A1 * | 6/2005 | Tarlow | 7/110 |
| 2007/0131706 | A1 * | 6/2007 | Jordan et al. | 221/197 |

FOREIGN PATENT DOCUMENTS

| | | |
|---|---|---|
| GB | PCTGB2012050459 | 3/2012 |
| WO | WO2011081402 A2 | 7/2011 |
| WO | WO2012117248 A2 | 9/2012 |

* cited by examiner

*Primary Examiner* — Stephen Vu
(74) *Attorney, Agent, or Firm* — Alfred M Walker; John F Vodopia

(57) ABSTRACT

A combination finger fold holder tong and surface texturizing set includes a set of tongs with finger pockets, whereby the pockets are movable towards and away from each other for grasping an article of food; plus a plurality of adhesively adherable sticker substrates having a first texture imparted side and an opposite adhesive bearing side with a release liner, whereby the texture containing adhesively adherable sticker is placed upon the food engaging surface for manual grasping of articles of food.

25 Claims, 18 Drawing Sheets

SIDE VIEW

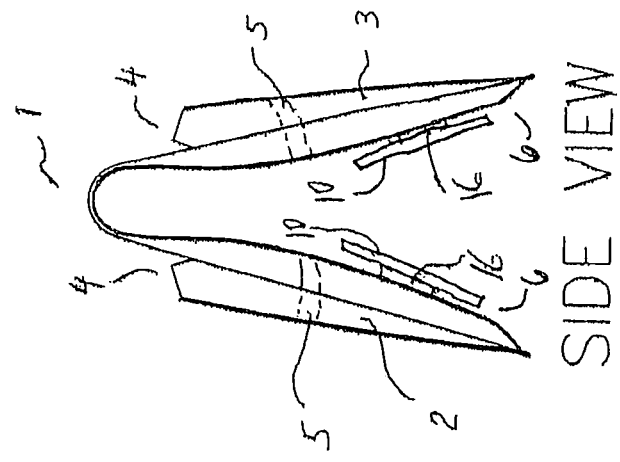
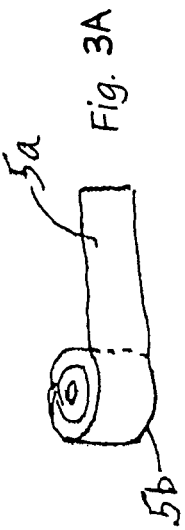
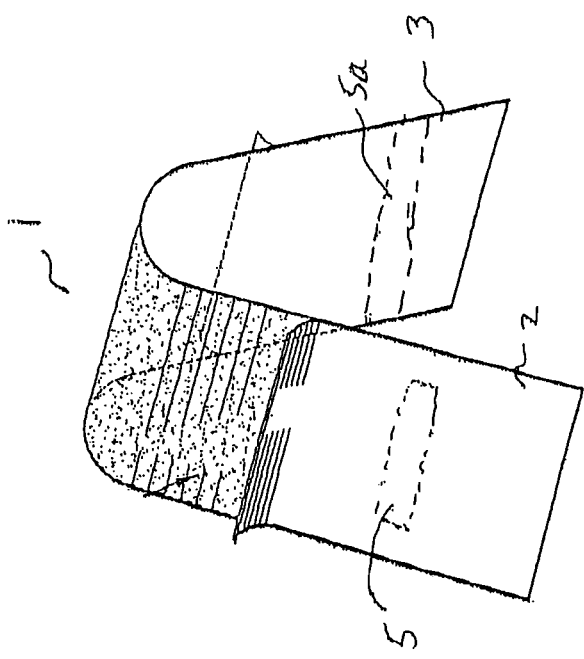

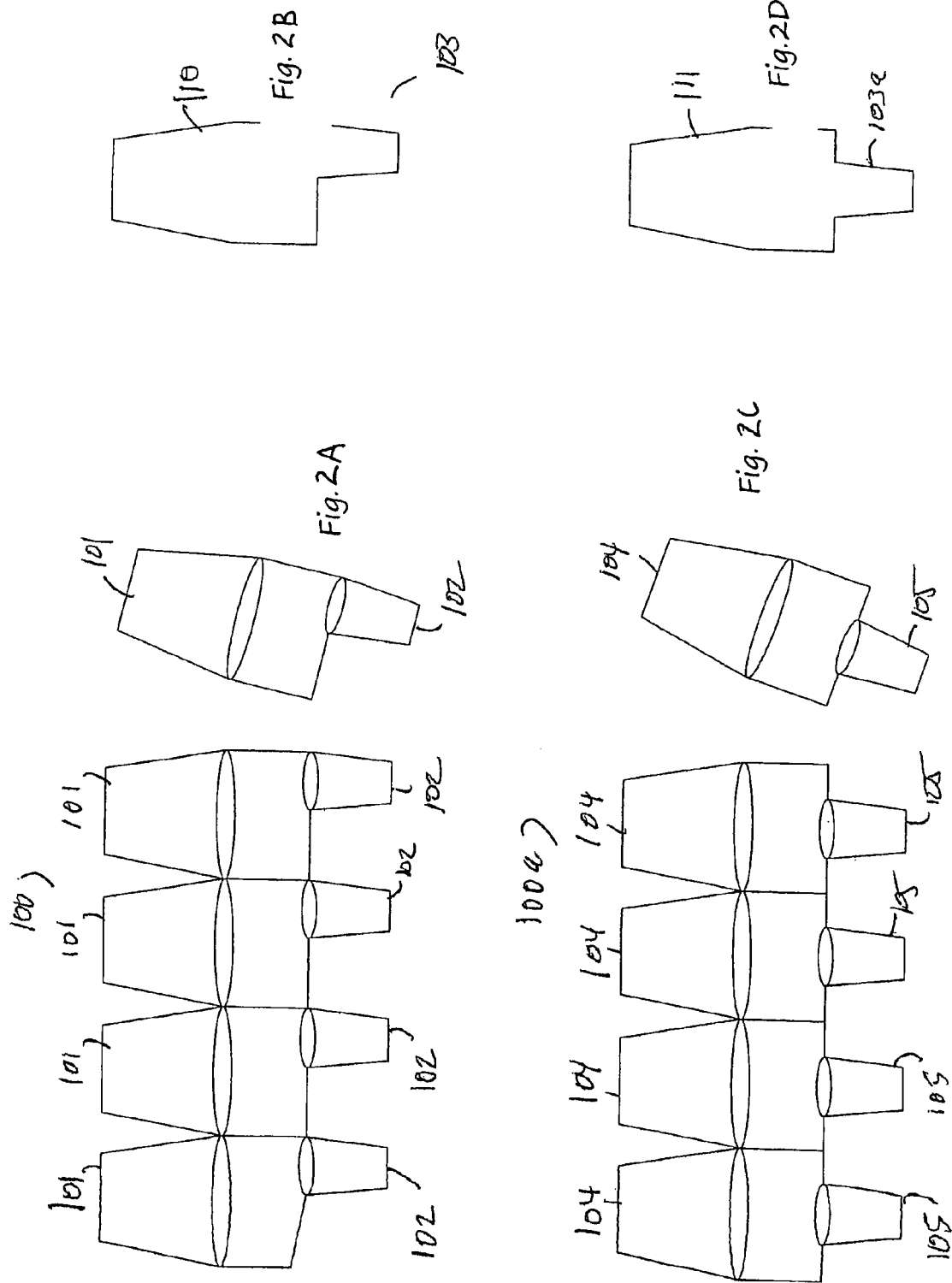

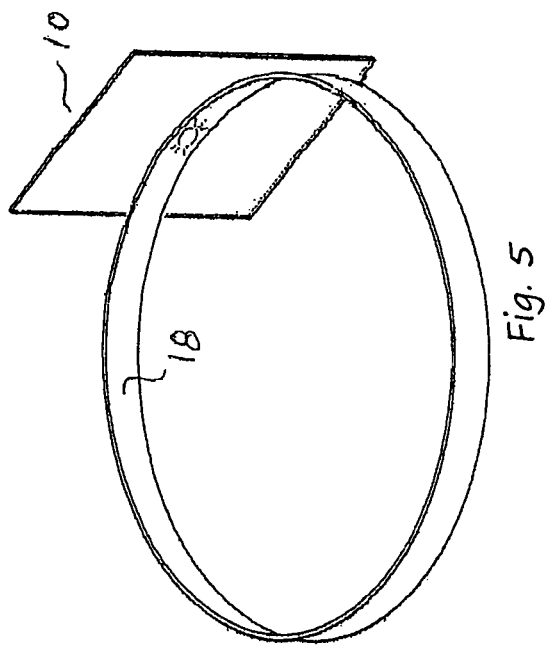
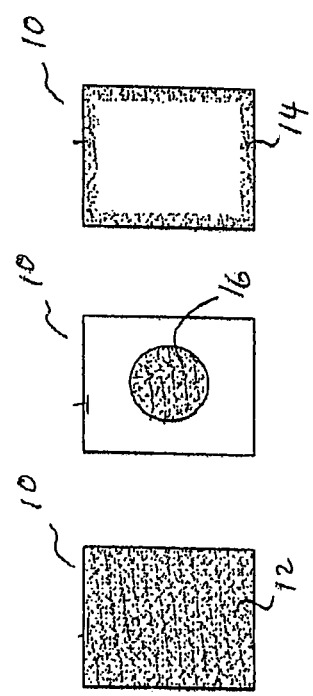
Fig. 5
Fig. 4

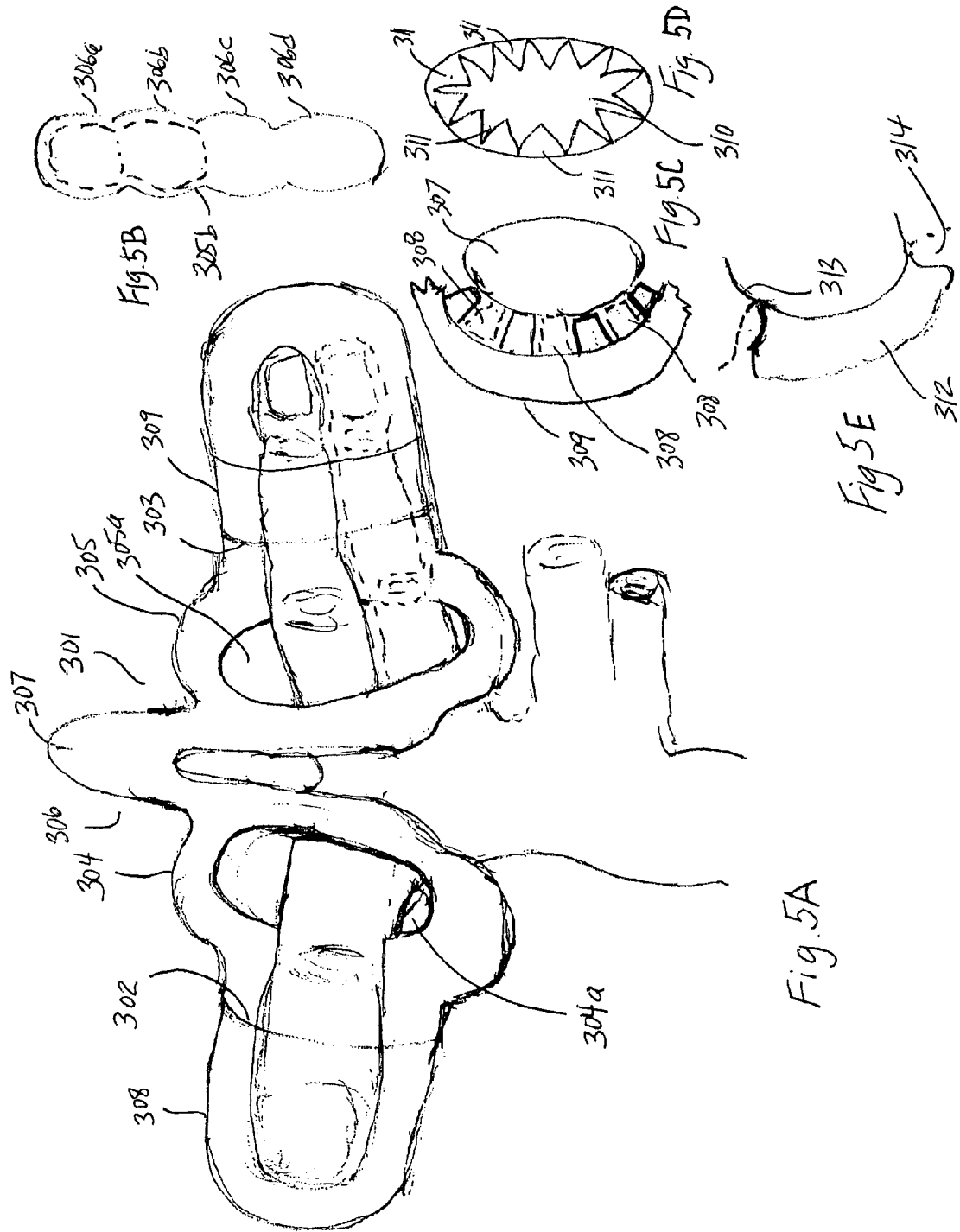

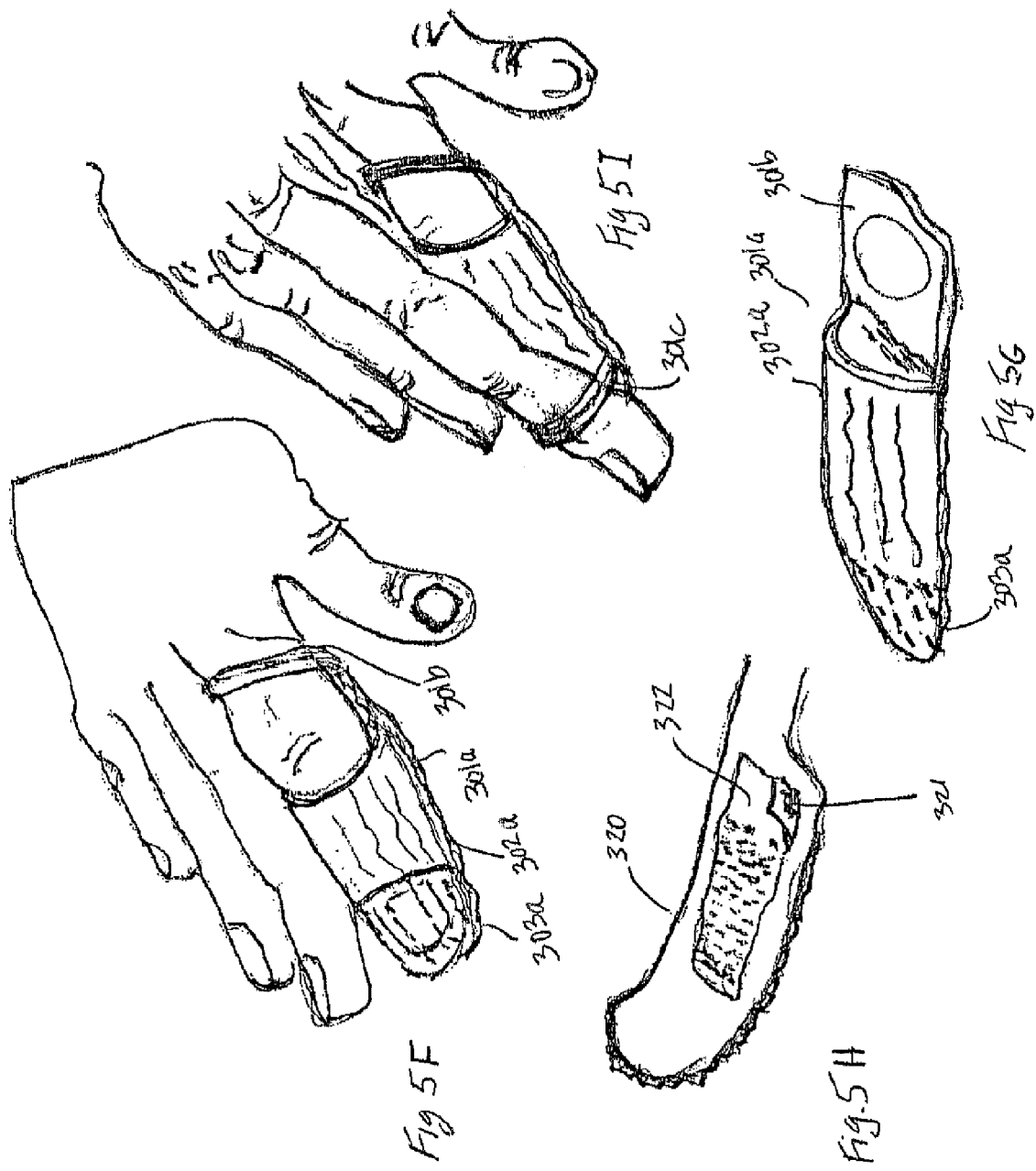

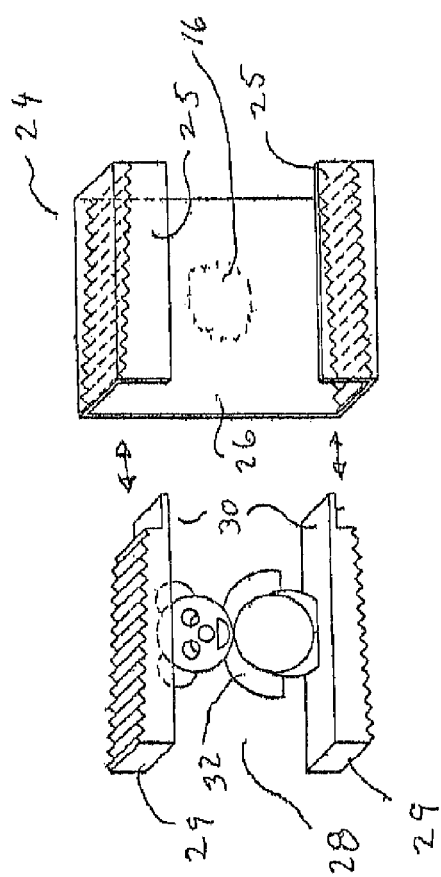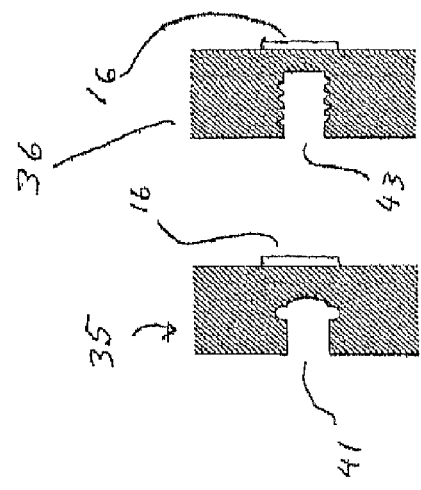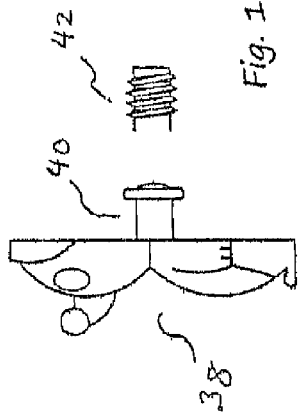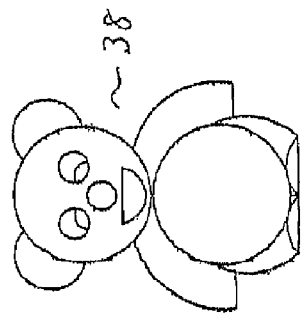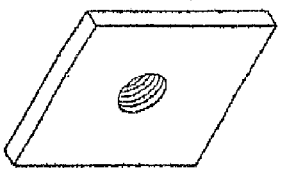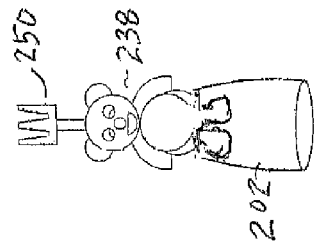

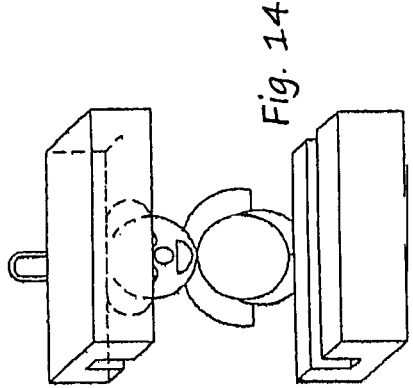
Fig. 14
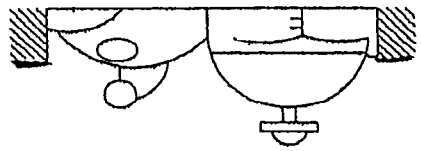
Fig. 16
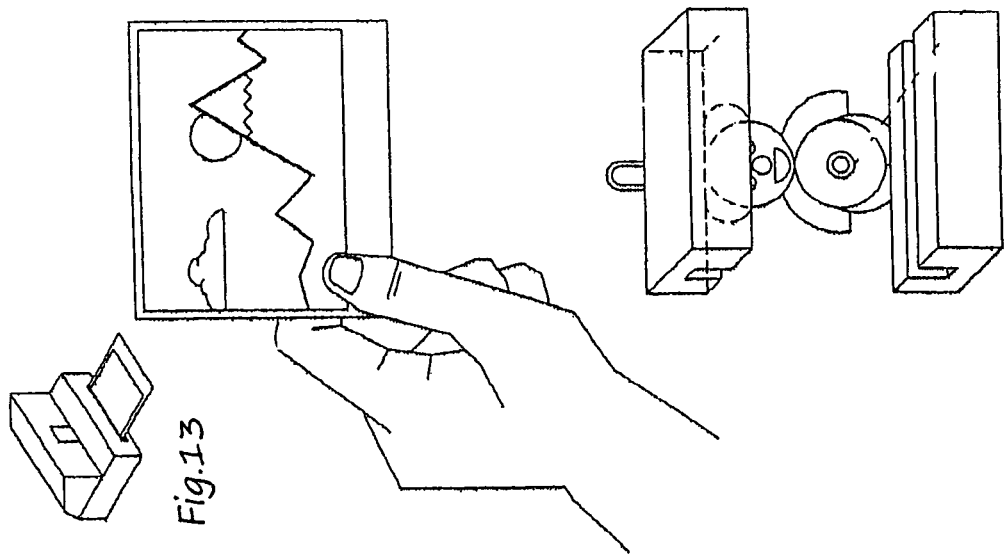
Fig. 13
Fig. 15
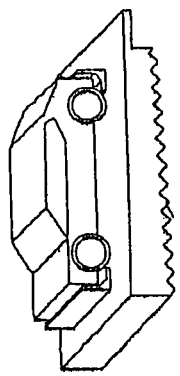
Fig. 12

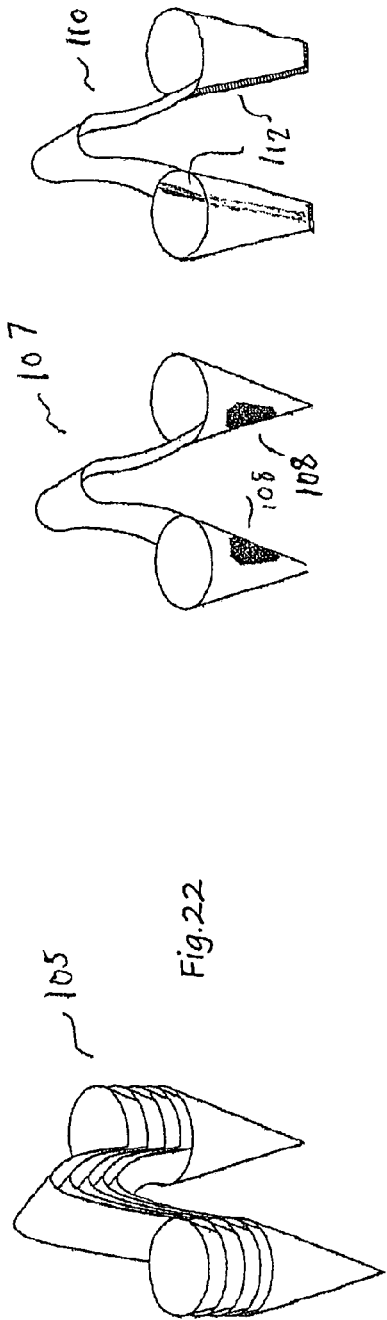
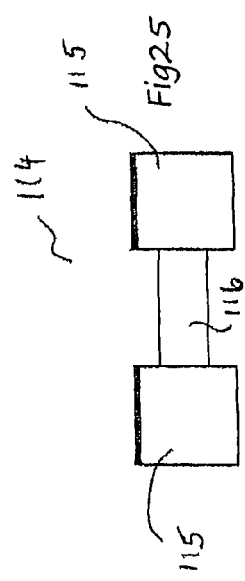
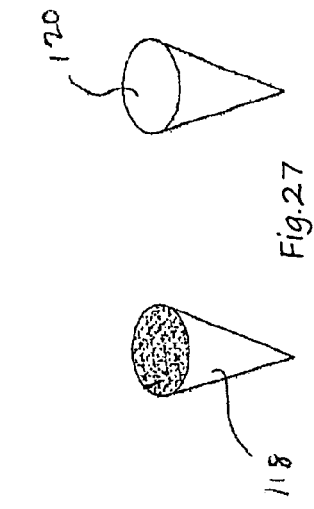

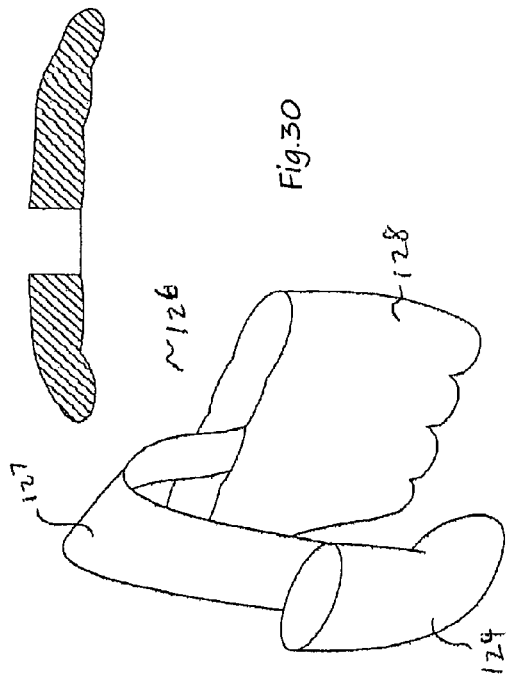
Fig.30
Fig.28
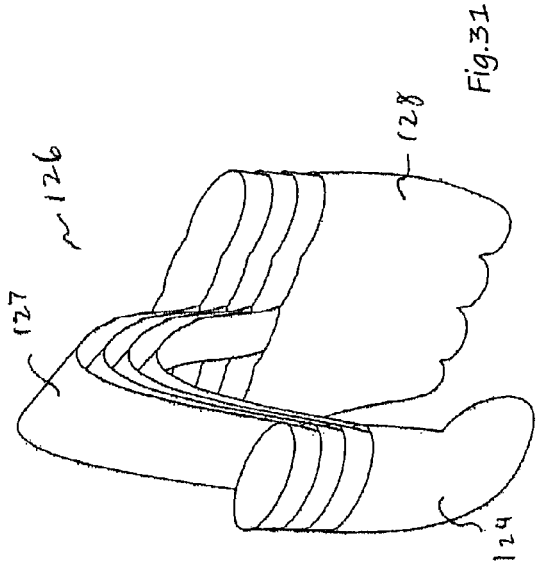
Fig.31
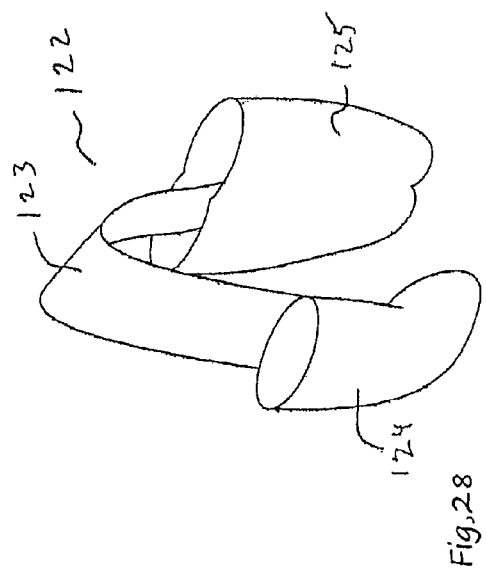
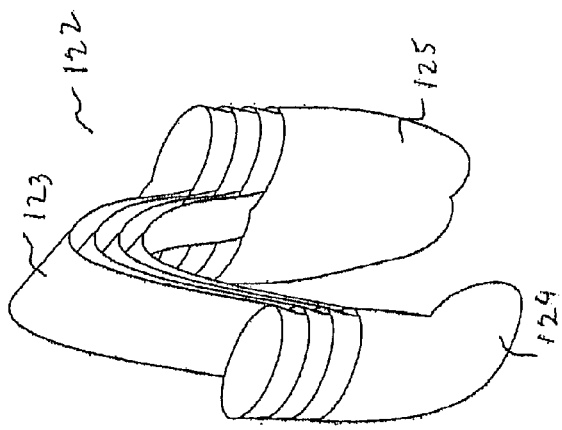
Fig.29

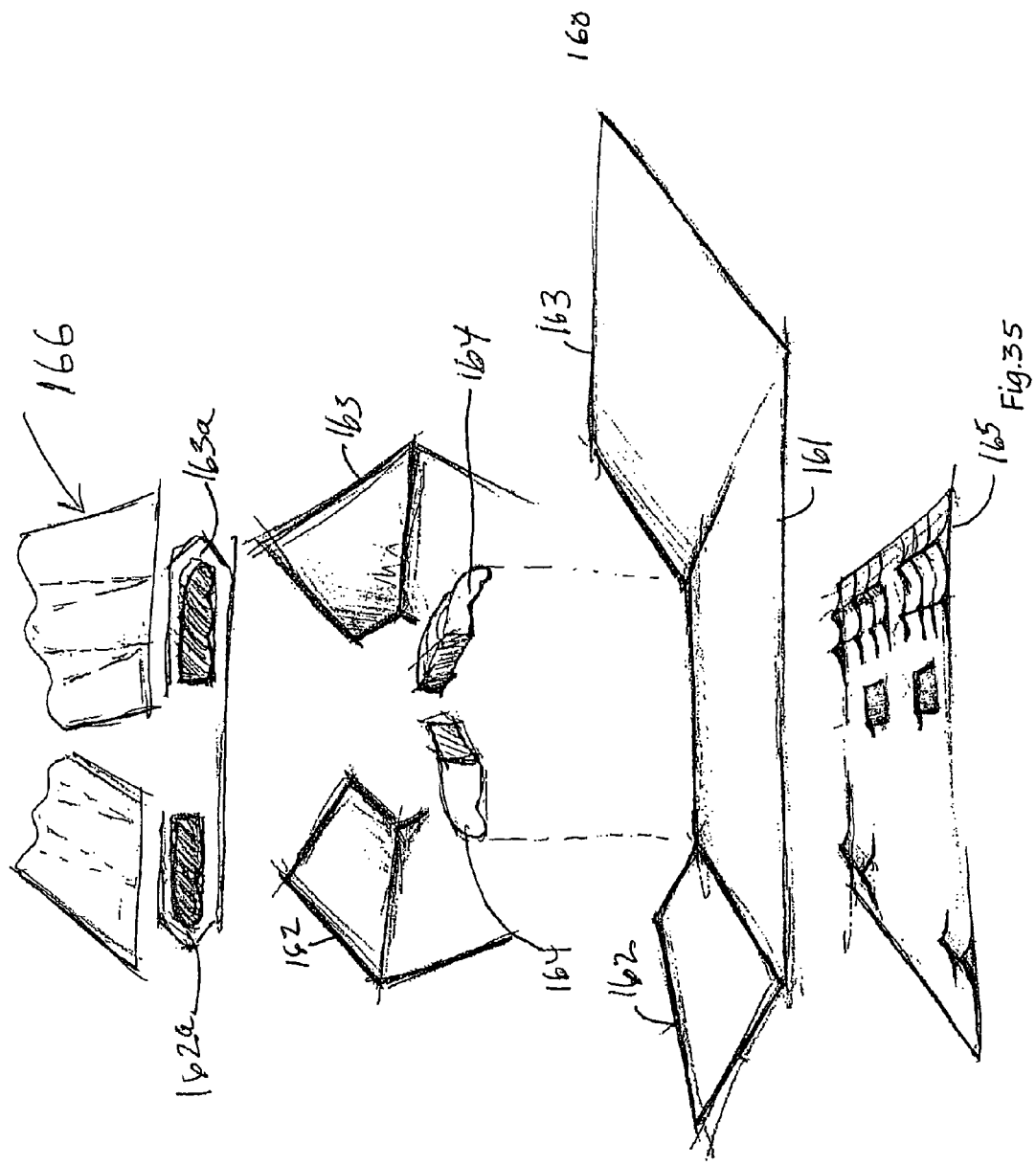

DISPOSABLE FINGER TONGS FOR HANDLING A FOOD PRODUCT

FIELD OF THE INVENTION

The present invention relates to disposable finger food holder tongs with enhanced grabbing and reduced tearability.

BACKGROUND OF THE INVENTION

Known prior art is the enclosed U.S. Pat. No. 5,848,928 of Wong which describes finger food tongs ("eating utensils") with texturized surfaces, but they appear to be permanently attached, not attached manually in situ by adhesive stickers.

Disposable paper based finger food tongs are described in the Jones, U.S. Pat. No. 3,407,927. However, Jones merely discloses folding a sheet of paper or plastic material to form opposite pockets with mid-facing pocket openings, which are not sealed for sanitary use, and then heat sealing or adhesive gluing of the left and right ride edges of each pocketed food holder before being cut into separate food holders. Jones also does not disclose adherable textured regions with free ends to permit pivoting.

Kaufman, U.S. Pat. No. 3,331,626, described finger tongs with open sided, unsealed pockets.

Known prior art also includes a recent pending European patent application number WO 2012/117248 of Ly from the United Kingdom of Great Britain which describes disposable paper finger tongs which are coated and textured for better gripping. However, Ly does not show the use of a central patch of adhesive on a central portion the back of the textured sticker patch to reduce ripping caused by full surface adhesive pulling against thin paper tong material. Ly also has complicated pleats to compress multiple folds to prevent unfolding of the pockets due to the resilient bias of his materials. However, Ly requires an extra long axis of the material to accommodate the folded pleats, as is clearly shown in Ly's FIG. 4, which excessively large areas 8 of adhesive, which are not required in the Applicant's present invention. Ly's fold lines are solely for the folding, not for sealing off Ly's pockets prior to use. Also, Ly's perforations are for scoring the edges of the pocketed handling implements, not for sealing off the finger insertion pockets prior to use.

OBJECTS OF THE INVENTION

It is therefore an object of the present invention to provide disposable finger food holder tongs with enhanced grabbing and reduced tearability.

It is also an object of the present invention to provide disposable finger food holder tongs with optional texturization.

It is also an object of the present invention to provide strong disposable finger food holder tongs with reduced tearing characteristics.

It is also an object of the present invention to provide disposable finger food holder tongs with optional shell cracker accessories.

It is also an object of the present invention to provide disposable finger food holder tongs with optional utensils.

Other objects which become apparent from the following description of the present invention.

SUMMARY OF THE INVENTION

The present invention comprises a combination finger food holder tongs set and surface texturizing set, which includes a set of tongs with finger pockets, whereby the pockets are movable towards and away from each other for grasping an article of food; plus a plurality of adhesively adherable or otherwise fastenable sticker substrates having a first texture imparted side and an opposite adhesive bearing side with a release liner, whereby the texture containing sticker is placed upon the food engaging surface for manual grasping of articles of food.

The disposable finger holding tongs for handling a food product include a strip of disposable flexible coated material having a central folded region. Distal ends of the strip form jaws of the tongs, with each distal end having a pocket to accommodate a finger, thumb or fingers of a user. A removable seal covers the disposable finger tongs prior to use; and respective textured surfaces are provided on grabbing surfaces of the jaws to assist in holding the food product. The textured surfaces may be crimped, embossed or formed in the surface of the jaws of the tongs, or may be provided on adherable stickers or substrates attachable to the jaws of the tongs.

Optionally a one side edge of the strip has perforations so that the tongs are separable from an adjoining strip whereby a plurality of the strips are formed from a single sheet of disposable flexible material, the strips being separable by the perforations. The perforations when using a single foldable sheet must be double perforation lines which will extend perpendicular to the axis of the aligned tongs, and located parallel to and close to the pocket mouth. The tong pockets each are sealed for sanitary purposes. When used, the perforation lined regions are pulled to reveal the open pocket from under the sealed portion.

Preferably each pocket contains an elastic or stretchable finger contact member, such as a length of elastic or stretchable strap or ring inside and/or outside of the pockets of the tong jaws, for maintaining an opening into each pocket to assist in holding the tongs upon the respective fingers and thumb of the user.

Optionally, at least one of the jaws has a food handling tool extending from a bottom end or other position place thereof, such as a fork, knife, spoon or chopsticks.

The tongs are formed from a sheet of flexible material, such as paper, plastic, fabric or combinations thereof, in which strips of the flexible material form respective tongs, in which a side edge of the strip has perforations so that the tongs are separable from an adjoining strip whereby a plurality of the strips are formed from the single sheet of disposable flexible material, the strips being separable at the perforations. Optionally, one of the jaws has separate pockets adapted for individual fingers of a user.

The tongs may also be adapted to be stackable.

The textured substrates or stickers preferably include a textured food engaging side and an opposite tong engaging side, the opposite tong engaging side having a centralized adhesive region surrounded by a non adhesive peripheral region with pivotable free ends, which are not contacting the opposite tong engaging side, to reduce the possibility of the adhesive pulling and ripping the tongs during use.

In another alternate embodiment, the sticker is attached to an elastic or stretchable ring, the elastic or stretchable ring being insertable over a respective tong of the tongs for engaging the sticker to the tong. Preferably the length of strip or ring (which optionally may be formed from two strips joined at the ends to form a closed ring) is elastic, so that when the finger enters the elastic expands and then tightly retracts upon the finger, whereas if the ring or strip(s) are instead stretchable, they will stretch when the finger is contracted, but will not retract thereafter.

In yet another embodiment, the sticker further comprises a three-dimensional C-side shaped immovable jaw member having a set of over hanging immovable jaws and ridges on the top and bottom inner surfaces thereof. The set of tongs may also have an accessory shell cracker or utensil bearing toy removably attachable to the three-dimensional C-side shaped immovable jaw member.

The disposable tongs may be produced by the method of coating a flat sheet of paper with a pre-perforated top layer, heat sealing the paper and, a) cutting the sheet at peripheral edges to form individual tongs, or b) tearing the sheet at the perforated regions, also at peripheral edges, to form individual tongs, and providing the tongs thus formed with textured food grabbing surfaces.

It is noted, however, that in a preferred optional embodiment, the tongs of the present invention also may have other perforations which are perpendicular to the lengthwise axis of the tongs, at least in the mid connecting tab region where the open mouths of the pockets are located and preferably sanitarily sealed before use, so that a sanitary cover seal can be removed along these perpendicular perforations, to reveal the openings of the pockets of each jaw of the tongs for finger, thumb or fingers being inserted into previously sanitarily sealed regions, extending at least in the central region between the pocket openings (or optionally, extending along the entire region or portion thereof of the flat tongs before use).

The tongs may be provided in a multiple stacked relationship, the stack of tongs being supported upon a stand having a base, a column and a clip, or on a hook extending from a wall, to hold the plurality of tongs Optionally, the tongs may comprise conical members formed from a sheet, the sheet wrapped around to form the conical shape at a sealed linearly extending joint, the sealed joint being provided in such an amount to provide a linearly extending textured food grabbing linear portion. The conical tong members may also be formed from a sheet, where the sheet is wrapped around to form the conical shape, the conical members each being provided with respective three dimensional crimped portions forming the textured food grabbing surfaces.

In another alternate embodiment, the disposable finger holding tongs for handling a food product include a strip of disposable flexible coated material having a central folded region; wherein distal ends of the strip form jaws of the tongs, each distal end having a pocket to accommodate a finger of a user. A removable seal may cover the disposable finger tongs prior to use and respective textured surfaces may be provided on grabbing surfaces of the jaws to assist in holding the food product. In this embodiment, the tongs are formed from a folded sheet of flexible material folded over a set of female dies (or at least one female die) pressed by a set of male dies (or by at least one male die) to form crimped open three dimensional finger and thumb portions (and finger joints) with textured surfaces, the folded materials and the dies being provided under a shroud providing a heat sealing of the tongs. The dies can also form crimps to for three dimensional surfaces corresponding to the palm area of the tongs.

In yet another alternate embodiment, a disposable food grabbing accessory includes a flexible substrate having a flat skin contact side and an opposite textured side, the flexible substrate being attached to an elastic or stretchable band placed over a finger. The textured substrate is attachable by the tensile force of the elastic or stretchable band extending over the finger, wherein the elastic or stretchable band directly holds the textured substrate directly on the finger.

In general, the present invention is a dispensable and retrievable container/system with sanitary paper tongs in a package in relation to the dispenser and a transferable sticker in a container, with a silicone release backer. Adherable texturized stickers are provided for handling lobster and shrimp surfaces needing abrasive rubbing thereon, but which do not touch skin. This invention relates to disposable tongs which are more particularly intended for use in handling unwrapped foods, for example, in shops, restaurants, although the tongs may, if desired, be used in suitable other cases where it is desired to avoid touching substances, such as medical or pharmaceutical particles to be picked up by hand.

A common method of handling foods in an unwrapped condition in shops is to use metal/plastic tongs, which may be used a considerable number of times in the course of a day's trading between cleanings. This is a disadvantage from a hygienic point of view, particularly as in the course of such use, the food-gripping surfaces of the tongs may inadvertently be handled or soiled and disposable sanitary paper an tear under moist conditions when pressure is applied to it and in contact with rough, sharp, pointed surfaces. An object of the present invention is therefore to provide tongs suitable for the use in handling food and food surfaces which can be produced at a cost sufficiently low to make it practicable for the user to throw them away after using once only.

Another objective of the invention is to overcome the tearing of the cost effective, disposable tongs. When a full glued base sticker is applied to paper tons, it can grab multi surfaces well, but paper tongs tear when pressure is applied to any one particular side. It causes the side of sticker with no pressure to lift, therefore pulling on sanitary paper causing tear and tears occur faster as the paper tongs get moist from food. In a preferred embodiment, to overcome the tearing and still provide a cost effective and practical disposable paper tong, the textured sticker has a central glue base only with the glue at the center of the base of sticker. It allows for the maximum grasping of the food surface and when pressure is applied to any one side of the sticker, the central glue adhesive region allows for a pivoting of the free peripheral ends of the sticker, because the outer base of the sticker is free of glue, which does not stick, is not connected it to the paper, which eliminates the pulling and tearing.

Although a fully glued base or a particularly outer perimeter glue (to save on glue) base can be applied to stronger, more expensive coated, plastic, multilayer, disposable, non-disposable tongs. According to the invention, the stickers and tongs can have optional three dimensional multi surfaces with self-locking, press in novelty or shell cracking accessories or more preferably, a zip track, wherein an accessory is pushed in and permanently locks for rugged use and safety (not necessary for connecting tab). Also, the accessory can be locked in place by fasteners, such as drawer fasteners or jewelry clasps.

According to the invention, stickers can be made in plastic injections, moldings and embossed sheet systems. Disposable tongs are formed, made by a strip of paper or other poly coated or other flexible, disposable material. By folding and heat sealing, gluing and cutting, there are different methods of producing hygienic, disposable tongs, with a high volume label press, leaving a perforated top pocket connecting tab which completely seals pockets and only when the top perforated tab is torn of its, exposes the bottom pockets' connector tab and reveals the mouth of the pocket. A preferred method is a strip of paper or flexible, disposable material, which is provided at each end with a pocket and is folded about its middle so that its pockets' ends form a connecting tab so that each pocket is at the outside of the tongs and has its mouth presented towards the middle of the strip, whereby the tongs can be held in use by the user inserting a finger or fingers into one pocket and a thumb into the other pocket. Also according to the invention, a plurality of disposable tongs can have a perforated connected ability at its ends or sides with or without perforated hygienic tab. (which does not have to be perforated.)

Connecting tongs can be provided in a boxlike dispenser that when pulled, a cutter on the dispensing box will cut a perforated connecting tab. Also the tongs thus produced can be stacked where the food touching side is faced down on a convex base, which allows for the pocket mouth to face up and open. Wheel allows the user to easily insert thumb and finger(s) into pockets.

Also according to an alternate embodiment of the invention, a convex, rectangular base, with two posts at each end can hold sets of tongs, which are placed on the convex base with a hygienic tab up with distal pocket tips in between posts. The narrow sides of rectangle are free moving, of whichever sides up and down so that the two narrow corner posts rest upon the distal tips of pocket. The weight holds tongs in place so tab can be torn off, exposing respective pockets' mouths and connecting pockets' tab, insuring that only that particular user will put their fingers and thumb into that particular tongs, and none others.

The open mouth, disposable tongs can be produced in current methods of using a production press and filling the tongs in a dispenser container. Preferably the tongs are flexible, with at least one textured surface substrate or sticker adhered thereto, and which does not touch the skin. Without limitation to other embodiments foreseen by this disclosure, to recapitulate, the important salient optional features of the textured food or other item handling tongs with in situ applied textured stickers (or in situ applied other textured bearing members) include at least as follows:

A. a textured sticker with a central glue adhesive back, a textured multilayer sticker, with at least one zip lock tracks,
B. at least one novelty or shell cracker or utensil accessory which locks into a sticker having three dimensional support members,
C. at least one textured sticker with an elastic or stretchable rubber band which goes over tong to hold a textured sticker in place without adhesive contact with the tong.
D. at least one textured sleeve jacket goes over the tongs,
E. a completely sealed (or partially seal) tong before use can have a peelable, perforated release tab to keep the inside surfaces of the tong recesses free of contaminants. When peeled, there are revealed recess pockets.
F. at least two tongs, joined together with a tearable, perforated connection.
G. an open, weighted dispenser for a plurality of tongs manufactured from a single sheet of flexible material, with pre-perforated separation lines therebetween.
H. A pull dispenser with connected tongs for dispensing tongs.
I) All tongs can be rounded, angled, shaped into a finger(s), etc., all can be covered with poly coated material, of a flexible material, such as paper, plastic or fabric, or combinations thereof, and can, coated on both sides, multi layered, with paper, material wax, synthetic wax and poly wax. A minimal margin to no margin can be created by adjusting the position of the fold lines of the paper or coated poly, flexible material, where the pockets' sides are a natural fold and seam of flexible material and seal, at locations, such as, for example, on bottom of pockets and on top or bottom center, like a manila envelope.

The preferred textured sticker to start with a predetermined design so when the user's thumb meets fingers, it mimics a bird beak to pick up pieces of food, such as meat or other food products, to be grabbed and consumed.

The tongs can have more than one sticker with protruding, abrasive textures, and the texture can be of a fanciful but abrasive texture, such as the face of a character, such as a design where two stickers meet to make a character on the tong's surfaces.

A male part on open sticker can insert into another sticker's female part when two stickers become hinged or solid locked, with an ability to become a fanciful and/or functional accessories, such as characters which can function as shell crackers.

The textured stickers can be embossed with a product such as known as poly 2301 Pioneer WI54868, 800-319-2477-751-234-9186.

The tong's pockets and respective food touching surface and/or entire back and front can be coated, printed, dipped, etc. in rubber, plastic, acrylic, etc., with or without pieces of crushed nutshell, processed corn bits, etc., to create a gripping surface with a bonding ability, that is sanitary and digestible.

Exterior paper on the bottom of each pocket can be shorter on top or back of each tong pocket so that a finger and thumb can find themselves into the recess of the pocket because the pockets can be provided with a different size of material on each side and top opening of pocket on food touching side where meets the tab, which may be longer than the back or pocket. This allows for easier finding of the openings of each pocket of each tong. A shorter back side can still be sealed, glued, etc., anywhere on the respective folded edges thereof.

In the coating process, a multicoated paper, such as aluminum is coated with paper, and then the paper is coated with poly wax.

In this process, at least a portion of the product can have textured, coated, multi coat surface.

Although adhesives, glue and heat sealing can be used, a cold seal method can also be used. Additionally joints can be sealed when the flexible material forming the tongs is rolled, crimped, sewn, knurled, etc.

Coatings help strengthen the paper tongs, which when used, break down quickly, with use and handling food A paper water shield can be added from the minimum amount to the maximum amount to get the tong stronger when it's wet. Water strength depends upon the amount of adhesive sprayed on at the time of turning pulp.

Multiple coatings can be applied with or without increased water resistance strength. The more adhesive applied, the more crinkly the paper is, which is undesirable for a napkin use. But in the use of a finger tong, it will add a needed strength to hold up against moisture and to keep the ink print on paper. Without the paper strength, any indicator or decorative ink tends to dissolve into the tissue, which then grossly dissolves into foods, although food-compatible, non-printed, coated material can touch the food.

Tongs can also be made with material such as used in making paper towels, i.e., for example, paper of two plys or more, or one ply paper. Although Kraft chemical pulping adds more dry strength by allowing chemical bonds, which can be enhanced with more dry strength additives, such as cationic starch in the form of bleach, bleach pulp of a paper napkin tissue, but it may still need wet strength by the aforementioned coating. Although wet strength and process are still in the experimental stages in the chemical pulp, wet strength additives such as polyamidoamine-epichlorohydrin resins may be added at a point in processing where the pH level is good, such as between 6-9, is then mixed with good negative charged amounts and without excessive positive charge when adding resins. In some cases, cationic wet strength resins can be improved by adding carboxymethykellulose or other negatively charged additives.

Heat or glue sealers can make the tongs of any be any size or geometric shape, with a function, for example, the tongs may be sealed in the shape of being rounded around fingers and/or thumb and in front of or tips of fingers or thumbs. This will allow for when fingers and/or thumb grab an article of food or other item. It allows for the things to be grabbed by the tongs, as the jaws of the tongs are brought together by the fingers and thumbs acting cooperatively. This creates a region for food grabbing, which helps hold on to food within a contoured conformational shape around the food article being held therein.

The tongs can be sealed anywhere to create different food nesting shapes. The jaw pockets can be equal sized, or two different sized pockets or one universal pocket, where the user places the pockets over both the thumb and finger to grab foods. The tongs are coated to form a stronger material to hold up against moisture-laden foods, for example, moist fruit salad or chow mein, to prevent the tongs from breaking down and dissolving into foods that are moist.

Each tong's pockets' respective seams can be provided on the outside and/or on the inside of the tong's pockets, which can have a seamless edge, frayed edges and/or edges cut in any shape or shapes, or turned inside out, like socks with an air suction method or other methods.

Each set of foldably joined tongs can have multilayer paper and/or poly plastics with poly or paper in between and/or poly coated material to stop grease penetrations. With heat, glue or other sealer, the closed end of the pockets are sealed, but the open ends can be opened from a sealed state where the user tears a perforated line of the tongs, either partially or fully around the tongs, to remove a sanitary seal covering the pocket opening of the jaws of the tongs, which the user removes, which reveals the pocket for insertion of the finger, fingers or thumb therein.

If made of paper the tongs can have wet strength glue that is poly based and other additives that are food compatible, but of synthetic and/or natural material, and which may be coated or not coated, such as by being embedded in the paper material to be folded and formed into the tongs.

Mylar, which is more flexible than paper, more durable and has an oil resistance feature, can be used as an alternate embodiment for the flexible sheet material, from which the tongs are made from.

An example of a machine for processing flexible sheet materials can be a FLEXO® machine, which is rotary-line operational. The optional permanent glue can be NCR ink adhesive. The flexible material may be MYLAR® (film) under the TYVEK®® trade name.

The Mylar material is processed in layers with adhesives, and cut to reveal a second layer When the tongs produced has a top connector (tab), the process of making is still the same, except in that the tab is left, then cutter cuts the material and adhesive is added.

To insert a drawstring from a reel of string, insertion starts at the beginning of the insertion process, then is placed in between sheets before a needle pulls through a length of the draw string to form a pull string which then can close the mouth of pocket, until opened by the user to reveal the finger insertion recesses in the tongs, or just pre-sewn into the material.

Optional steel dies can start the tong forming process for three dimensionally shaped tong pockets process, which are then optionally crimped or otherwise shaped to provide the textured surface, which can be a pattern, a random accumulation of texturization, or can be contacted with a glob, or squirt of silicone glue placed on the food grabbing side of the tongs, which glob of silicone is formed into shapes, tools, logos, characters, which are then adhered to the surface texturization of the tongs.

BRIEF DESCRIPTION OF THE DRAWINGS

The present invention can best be understood in connection with the accompanying drawings. It is noted that the invention is not limited to the precise embodiments shown in drawings, in which:

FIG. 1 is a perspective view of one embodiment of the tongs of this invention showing the location of an elastic or stretchable member in each finger recess to aid in insertion, tight fit and withdrawal of a finger from a recess, wherein the elastic or stretchable member can be one or more elastic or stretchable strips inside or outside of each finger/thumb insertion tong, or can be a closed loop ring, either formed by joining two linear strips at respective end pairs, to form a closed loop when two laid parallel strips are on a folded portion of a sheet of material and the fold line is parallel to each strip, whereby folding over the intermediate fold line causes the strips to lay co-terminus on top of each other, where they are spot sealed at each end to form a closed loop, or alternatively, a prefabricated ring is inserted flattened into each tong and sealed in location at opposite ends thereof. Beaded glue will stick to the paper and allow for stretching.

FIG. 2 is a side elevation of the tongs of FIG. 1.

FIGS. 2A, 2B show strips of tear-off tongs with smaller offset open thumb accommodating portions and a knife and thumb forming region associated with forming same.

FIGS. 2C, 2D show strips of tear-off tongs with smaller centered open thumb accommodating portions, and a knife and thumb forming region associated with forming same.

FIG. 3 is a perspective view of the elastic or stretchable ring which is located by illustration in FIGS. 1 and 2.

FIG. 3A is a perspective view of an elastic or stretchable linear strip cut from a roll of elastic or stretchable material.

FIG. 4 shows a back elevation of a sticker with three variations of adhesive patch; full adhesive is shown in the left illustration, a central round patch is shown in the middle illustration, and a perimeter adhesive, seal or glue region is shown in the rightmost sticker illustration.

FIG. 5 is a perspective view of a sticker attached to an elastic or stretchable band capable of attaching the sticker to a finger recess by the tensile force of the elastic or stretchable band.

FIG. 5A is flat plan view of an alternate embodiment for a ring structure of material with finger insertion openings where two rings are joined by a strip region at a common edge, and have extending therefrom the textured finger grabbing portion, or use of a textured sticker as in FIGS. 4, 5 and 7. Optionally, sleeve pockets or holding bands can be added to the finger grabbing portion.

FIG. 5B is a top plan view of contoured die cut hole with contoured figure outline shapes of an alternate embodiment of the ring structure of FIG. 5.

FIG. 5C is a top plan view of an alternate embodiment for a cover for the ring hold of the ring structure shown in FIG. 5, with perforatable attachments to a holding band of the ring structure of FIG. 5A.

FIG. 5D is a top plan view of a ring hole with serrated or undulating projections to snugly grip a finger in the ring hole of the ring structure of FIG. 5A.

FIG. 5E is a cushioned layer overlapping an edge of the ring structure of FIG. 5A.

FIGS. 5F and 5G are perspective views of a single ring embodiment finger tool.

FIG. 5H is a detail view of an auxiliary textured tool attachable to a finger tool.

FIG. 5I shows an optional second ring 301c to hold a distal end of a second finer for stability and strength.

FIG. 7 is a perspective view of a three-dimensional multilayer sticker with a C-side shape and ridges on the top and bottom inner surfaces for accepting an assembly consisting of a toy temporarily attached to top and bottom ridged blocks which mate with those in the sticker.

FIG. 8 is a front view of a toy with a press-in protrusion on its back.

FIG. 8A is a front view showing a shell cracker with a utensil attached to a jaw of a pair of tongs.

FIG. 9 is a side elevation of the toy of FIG. 8.

FIG. 10 is a side elevation of a screw-engagement protrusion next to a perspective view of a flat sticker with a central threaded hole.

FIG. 11 shows two side cross sections of deep stickers, one with a central recess to engage a press-in toy and the second with a threaded central hole to accept a threaded protrusion on the toy.

FIG. 12 is a perspective view of a car toy attached to sticker-attaching base.

FIG. 13 is a perspective view showing a camera and a hand holding a snapshot created by the camera; this illustrates the option of creating custom art work for decorating a sticker surface.

FIG. 14 shows a perspective view of a toy engaged with a sticker having grooves on the inside of top and bottom protrusions.

FIG. 15 is a perspective view of a toy with a locket and handle engaged with a grooved sticker.

FIG. 16 is a side elevation of the toy and sticker of FIG. 15.

FIG. 22 is a perspective view of a nested stack of tongs of this invention having conical recesses for finger insertion.

FIG. 22A is a sanitary lid for insertion over the top cap of a stack of tongs.

FIG. 23 shows a perspective view of tongs with conical recesses having crimped facing food-contact areas.

FIG. 24 is a perspective view of tongs with truncated cone finger recesses with facing crimp seals which form the food contact areas.

FIG. 25 is a flat plan view of a flat cutout which can be formed to produce tongs with conical finger recesses; two distal rectangular sections with a stripe of adhesive at one edge are formed into the cones.

FIG. 26 is a perspective view of tongs made from the plan cutout of FIG. 25.

FIG. 27 shows a perspective view of a coated paper cone and a conical heated mold used to bond the cone.

FIG. 28 is a perspective view of molded tongs with a shaped thumb recess and a two-finger recess attached by a strap section.

FIG. 29 is a perspective view of a nested stack of tongs of FIG. 28.

FIG. 30 is a perspective view of molded tongs with a shaped thumb recess and a four-finger recess attached by a central strap section.

FIG. 31 is a perspective view of a nested stack of tongs of FIG. 30.

FIG. 35 is an exploded diagrammatic view of the steps used in forming disposable flexible plastic or reinforced paper tongs with textured surfaces.

DETAILED DESCRIPTION OF THE INVENTION

Figure 6:
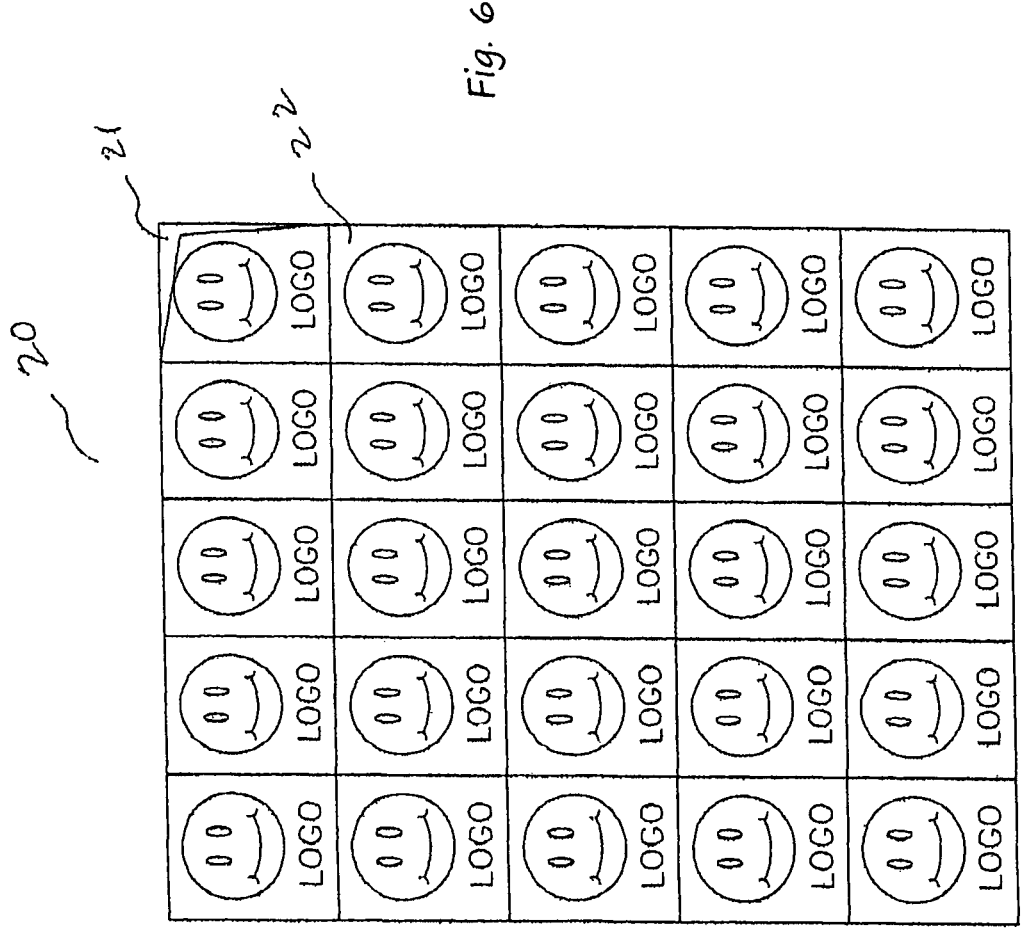
FIG. 6 is a top view of a sheet of kiss cut stickers with a fanciful indicia on a backing sheet for easy single peel-off.

The present invention has broad applications to many technical fields for a variety of articles. For illustrative purposes only, a preferred mode for carrying out the invention is described herein.

FIGS. 1 and 2 show one embodiment of the tongs 1 of this invention showing the location of an elastic or stretchable member 5 or 5a, such as one or more strips 5a or a ring 5 in each finger recess 2,3 to aid in insertion and withdrawal of a finger from a recess 2 or 3.

The tongs are formed from a flat folded sheet of flexible heat sealable material, such as coated paper, plastic, fabric or combinations thereof, such as cotton/polyester, or fabric strand strengthened paper, such as linen paper, for example. One side of a finger insertable tong can be made of one material, such as coated paper, and another side can be made of coated plastic or coated fabric. Each closed finger sleeve 2 and 3 has a closed distal region 6 and an open finger insertion region 4, with an optional draw string for tighter fit around the finger or fingers. The draw string can be pre-sewn, or sewn in during folding, heat sealing and cutting processes of producing the tongs. Die cut perforated holes at the mouth of each pocket can be imparted for improved stability of the tongs holding a finger, thumb or fingers therein. The elastic or stretchable member 5 or 5*a* can be one or more elastic or stretchable strips 5*a* inside or outside, or both, of each finger insertion tong, or can be a closed loop ring 5 inside or outside, or both, of each finger insertion tong. Ring 5 can be a preformed closed loop ring, which can be an in situ formed ring 5, either formed by joining two linear strips 5*a* at respective end pairs, to form a closed loop when two laid parallel strips 5*a* are on a folded portion of a sheet of material and the fold line is parallel to each strip, whereby folding over the intermediate fold line causes the strips 5*a* to lay co-terminus on top of each other, where they are spot sealed or spot/beaded glued at each end to form a closed loop ring 5, or alternatively, ring 5 can be a prefabricated ring 5 which is inserted flattened into each tong pocket recess 2 and/or 3 and sealed or glued in location in situ at opposite ends thereof, within the respective pockets 2 and/or 3. Additionally, the elastic or stretchable member 5, in the form of one or more strips 5*a* or one or more rings 5, can extend the full width of the jaw tong pocket 2 or 3, or, as shown in FIG. 2, can extend partially within each jaw tong pocket recess 2 or 3. As also shown in FIG. 1, either the ring 5 or the strip 5*a* can extend partially across the recess pocket 2 or 3, or can extend the full width of recess pocket 2 or 3. For example, FIG. 1, while not being limited in scope, shows elastic or stretchable member 5 extending partially across the recess pocket 2, and shows elastic or stretchable member 5*a* extending the full width of recess pocket 3. It is assumed that the reverse can occur, where either recess pocket 2 or 3 can have one or more interior or exterior partially extending or full width elastic or stretchable members 5 or 5, either as one or more rings 5 or strips 5*a*.

For sanitary reasons the flat folded sheet of coated paper has a release liner covering open regions 4 before use. Alternatively multiple elastic or stretchable straps may be used.

FIGS. 2A, 2B show strips 100 of tear-off tongs 101 with smaller offset thumb accommodating portions 102, and a knife 110 and thumb forming region 103 associated with forming same. FIGS. 2C, 2D show strips 100*a* of tear-off tongs 104 with smaller centered thumb accommodating portions 105, and a knife 111 and thumb forming region 103*a* associated with forming same.

In one embodiment shown in FIG. 3, internal ring 5 is attached within each respective finger recess 2 and 3 to press against the finger while the tong goes from a flat pre-insertion state to an opened billowed state with a finger, thumb or fingers therein. Alternatively the elastic or stretchable member 5 or 5*a* may be an internal elastic or stretchable strap instead of a ring. Optionally a second ring or strap can be provided on the outside surface of each tong, for better stability of the tongs over the finger, thumb or fingers.

FIG. 3A shows an elastic or stretchable linear strip 5*a* cut from a roll 5*b* of elastic or stretchable material, to be inserted as one or more strips 5*a* on the inside or outside of each pocket 2 or 3 of the tongs 1 of FIG. 1.

FIG. 4 shows a back elevation of a textured, food engaging sticker 16 with three variations of adhesive patch; full adhesive 12 is shown in the left illustration, a central round patch 16 is shown in the middle illustration, and a perimeter adhesive region 14 is shown in the rightmost sticker illustration. The advantage of central round patch of adhesive 16 is that it minimizes contact with paper finger recesses 2 and 3, so that free edges on the reverse food grabbing side can contact food without ripping the paper walls of finger recesses 2 and 3.

FIG. 5 shows an alternate sticker attached to an elastic or stretchable band 18 capable of attaching the sticker 10 to a finger recess 2 or 3 by the tensile force of the elastic or stretchable band 18. This embodiment can also be used without tongs, where the textured sticker is applied to a food grabbing side a finger while the elastic or stretchable band directly hold the textured sticker directly on the finger, wherein a disposable food grabbing accessory comprises a flexible substrate having a flat skin contact side and an opposite textured side. The flexible substrate is attached to an elastic or stretchable band placed over a finger, wherein the textured substrate is attachable by the tensile force of the elastic or stretchable band over the finger, so that the elastic or stretchable band directly holds the textured substrate directly on the finger, without any tongs.

FIG. 5A shows a flat plan view of an alternate embodiment for a ring structure 301 of material with finger insertion openings 302, 303 where two rings 304, 305 with holes 304*a*, 305*a* are joined by a strip region 306 at a common edge 302, and have extending therefrom the textured finger grabbing portion, instead of a textured sticker 10 as in FIG. 5. Optionally, sleeve pockets 308 or one or more holding bands 309 can be added to the finger grabbing portion.

FIG. 5B shows a die cut hole 305*b* with contoured finger shapes 306*a*, 306*b*, 306*c* and 306*d* for holding one or more fingers shown in dashed phantom lines in crossection.

FIG. 5C shows ring hole cover 307 connected by perforatable attachments 308 connectable to, and releasable from ring 309.

FIG. D is an alternate embodiment for ring hole 310 with serrated or otherwise undulating projections 311 to snugly grab a finger.

FIG. E is a cushioned layer 312 for edge 313 of ring 14.

FIGS. 5F and 5G are perspective views of a single ring embodiment finger tool 301*a* with ring 301*b* with band 302*a* and base 303*a* for finger insertion therebetweeen. Ring 301*b* helps keep the finger tool 301*a* upon the user's finger without falling off.

FIG. 5H is an auxiliary textured tool 320, such as a cake frosting knife, attachable by an adhesive 321 below a release liner 322 to a bottom of base 303 of finger tool 301*a*. Finger tool 301*a* can handle or manipulate food or money in a sanitary manner.

FIG. 5I shows an optional second ring 301*c* to hold a distal end of a second finger for stability and strength.

FIG. 6 shows a sheet of kiss cut textured stickers 22 with a fanciful indicia on a backing sheet 21 for easy single peel-off before insertion on the food grabbing surfaces of finger recesses 2 and 3 of disposable paper tongs 1.

FIG. 7 shows a three-dimensional multi-layer sticker 24 with a C-side shape a set of over hanging immovable jaws and ridges on the top and bottom inner surfaces thereof for accepting an assembly 28 including a child's novelty toy 32 temporarily attached to top and bottom ridged blocks 29 which mate with those in the sticker 24. The toy 32 can also function as a shell cracker or meat tearer accessory for cracking shells of food products, such as shrimp or lobster. The toy/shell cracker can be a collectable item adorned with famous characters or other decorations, amusement or restaurant themes and/or sports logos. Finger grips 30 enable detachment of assembly 28 from sticker 24.

FIGS. 8 and 9 both show a novelty toy or shell cracker 38 with a press-in protrusion 40 or threaded protrusion 42 on its back, engageable with a textured sticker 36 having a female recess engageable with protrusions 40 or 42 before use, when novelty toy or shell cracker 38 is removed from textured sticker 36. FIG. 8A shows a shell cracker sticker 238 with a utensil 250 put on and adhered to a jaw 202 of a pair of tongs.

FIG. 10 shows screw-engagement protrusion 42 next to a flat sticker 36 with a central threaded hole.

FIG. 11 shows two deep stickers 35 and 36, one with a central recess 41 to engage a press-in toy/shell cracker 38 with press-in protrusion 40 and the second with a threaded central hole 43 to accept a threaded protrusion 42 on the toy/shell cracker 38.

FIG. 12 shows a car toy/shell cracker attached to sticker-attaching base.

FIG. 13 is a perspective view showing a camera and a hand holding a snapshot created by the camera; this illustrates the option of creating custom art work for decorating a textured sticker surface.

FIG. 14 shows a toy/shell cracker 38 engaged with a textured sticker having grooves on the inside of top and bottom protrusions thereof.

FIGS. 15 and 16 shows a toy/shell cracker or accessory utensil with a locket and handle engaged with a grooved textured sticker. Optionally the toy/shell cracker/utensil bearing accessory can optionally extend forward with abrasive and/or protruding surface projections, so that it can also contact food, without being removed separately from the three dimensional texture bearing member.

Figure 17:
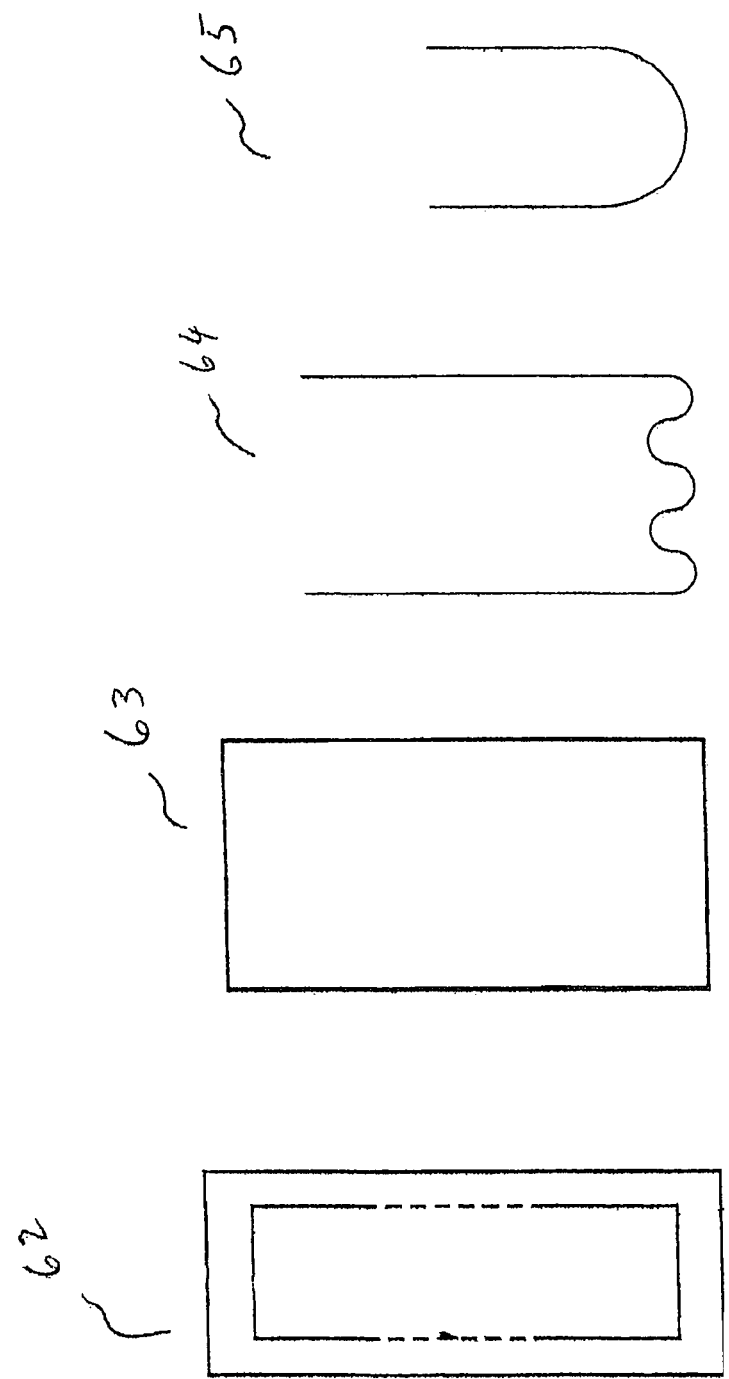
FIG. 17 is a plan illustration of four different heat sealers: double continuous sealer, rectangular sealer, wavy sealer, and semi-circular sealer.

FIG. 17 is a plan illustration of four different heat sealers: double continuous sealer 62 (or partial sealer), rectangular sealer 63, wavy sealer 64, and semi-circular sealer 65 used to seal the edges of tongs 1 with various geometric shaped sealed edges. Seals can be of any size or shape and can be double or multiple seals, to facilitate the tongs with a pair of pockets folding onto itself, to increase gripping edge area.

Figure 18:
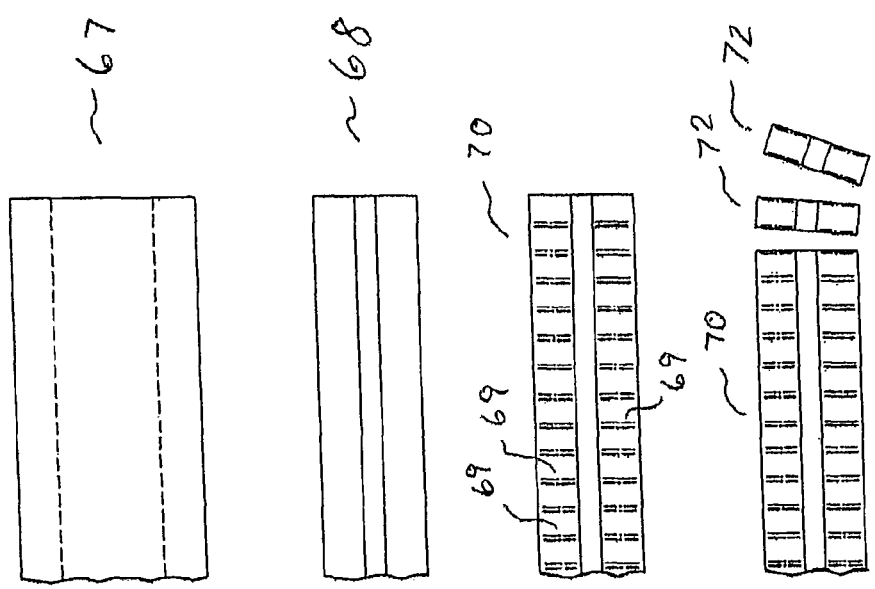
FIG. 18 is a progression of four plan images showing the prior art method of forming tongs by folding a flat sheet top and bottom toward the middle, heat sealing or adhesively bonding the fold-overs, and then cutting the individual tongs produced.

FIG. 18 is a progression of four plan images showing the method of forming tongs 1 by folding a flat sheet top and bottom toward the middle, heat sealing or adhesively bonding the fold-overs, and then cutting the individual tongs produced, including optionally fully sealed with double perforations provided for open pockets.

Figure 19A:
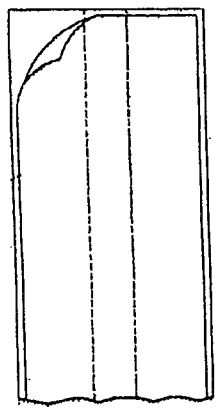
FIGS. 19A, 19B and 19C is a progression of three plan images of a two layer version starting with a flat coated sheet with pre-perforated top layer, heat sealing with optional draw string, and tearing at perforated regions to form individual tongs.
Figure 19B:
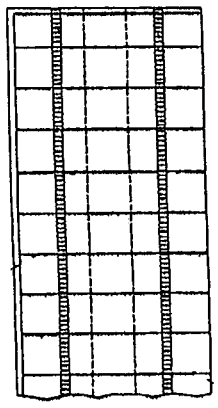
Figure 19C:
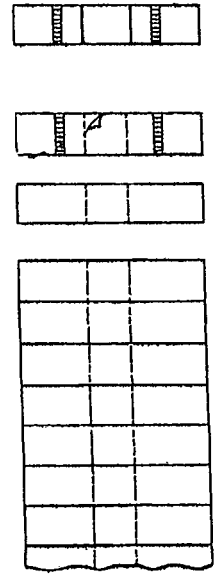
Figure 19D:
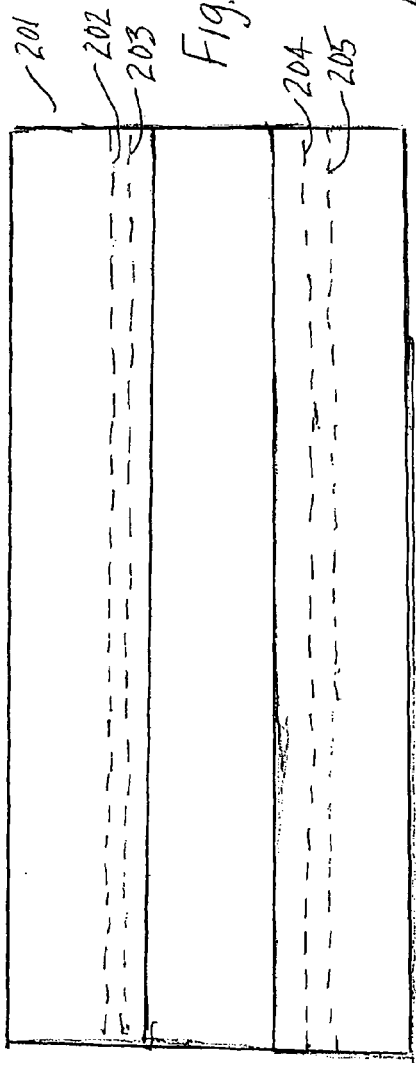
FIGS. 19 D, 19E and 19F show an alternate embodiment where the tongs are produced by only a single sheet of folded paper, as opposed to the two paper sheet layers of FIGS. 19A, 19B and 19C.
Figure 19E:
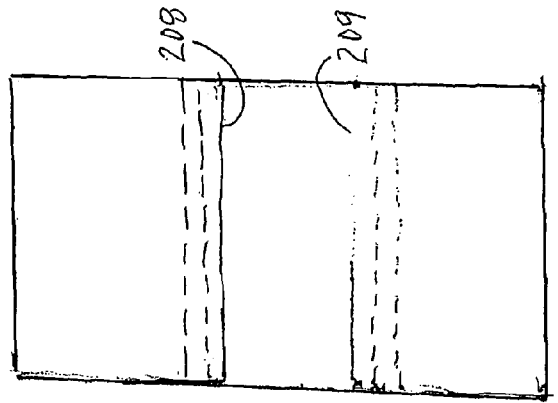
Figure 19F:
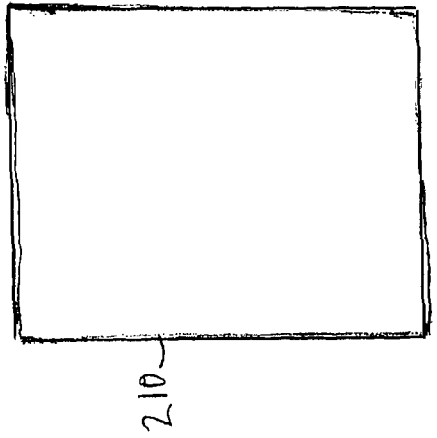

FIGS. 19A, 19B and 19C show a progression for a two sheet layer of forming tongs, with three plan images 19A, 19B and 19C starting with a flat coated sheet step 75 with pre-perforated top layer, heat sealing the paper 17 step 76 with optional draw string, and tearing sheet at step 77 at perforated regions to form individual tongs 1.

FIGS. 19 D, 19E and 19F show an alternate embodiment where the tongs 201 are produced by only a single sheet of folded paper, as opposed to the two paper sheet layers of FIGS. 19A, 19B and 19C. For example, optionally a one side edge of the strip has perforations so that the tongs are separable from an adjoining strip whereby a plurality of the strips are formed from a single sheet of disposable flexible material, the strips being separable by the perforations. The perforations when using a single foldable sheet must be double perforation lines which will extend perpendicular to the axis of the aligned tongs, and located parallel to and close to the pocket mouth. The tong pockets each are sealed for sanitary purposes. When used, the perforations lines are pulled to reveal the open pocket from under the sealed portion.

Figure 20:
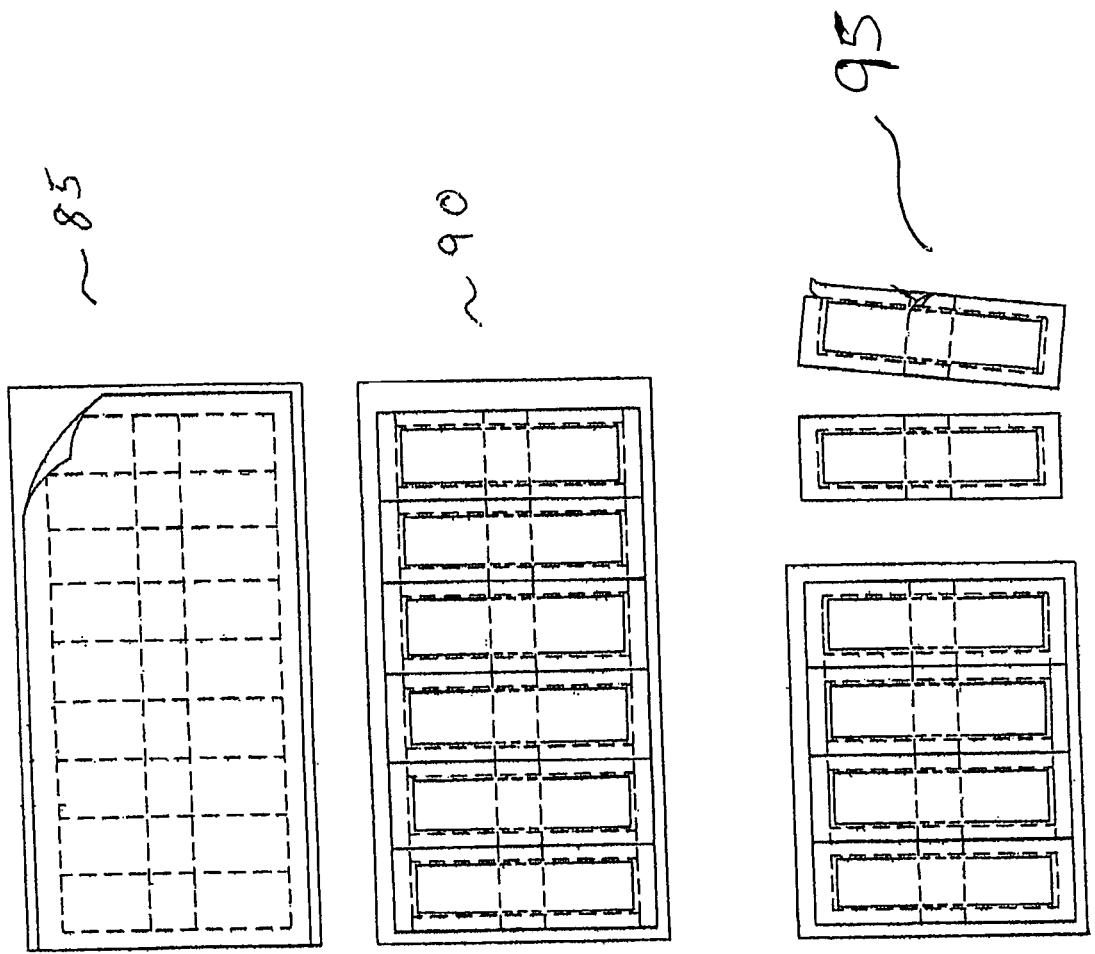
FIG. 20 is an alternate three step process (similar to that of FIG. 19) but producing tongs with border regions around each tongs to prevent choking of children.

FIG. 20 is an alternate three step process 85, 90, 95 (similar to that of FIG. 19) but producing tongs with border regions around each tongs to make tongs too wide for insertion into children's mouths, to prevent choking of children.

Figure 21:
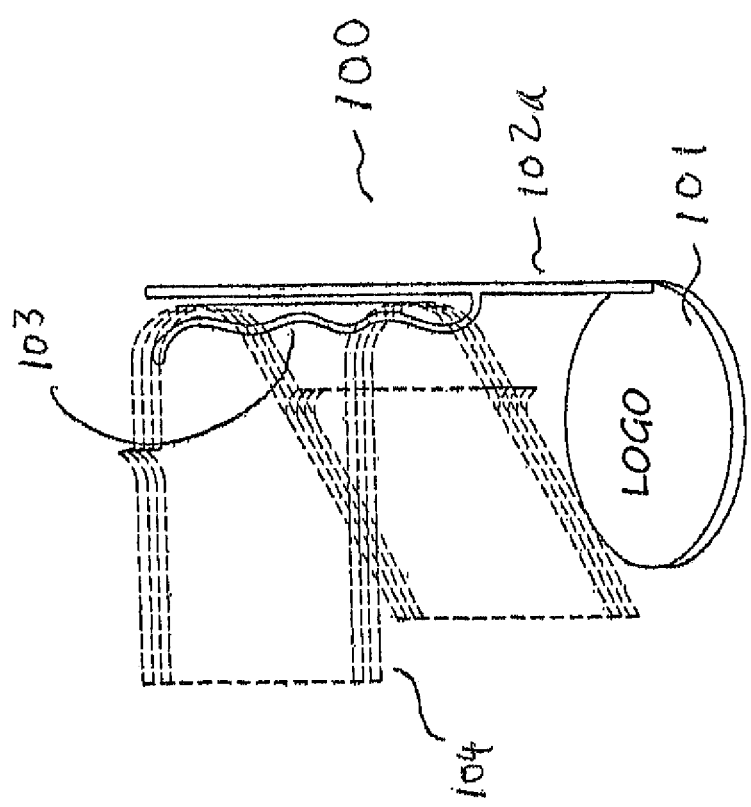
FIG. 21 is a perspective view of a stand with base, column, and clip to hold a supply of tongs on a tabletop.

FIG. 21 shows an alternate embodiment of a stand 100 with base 101, column 102a, and clip 103 to hold a stacked supply of tongs 1 on a tabletop. Optionally the support member for the stacked supply of tongs can be a wall mounted hook.

FIG. 22 shows an alternate embodiment of a nested stack 105 of tongs of this invention having conical recesses for finger insertion, which may have a lid cap for the uppermost tongs of a stack of tongs. FIG. 22A shows a sanitary lid for insertion over the top cap of a stack of tongs.

FIG. 23 shows a perspective view of tongs 107 with conical recesses having crimped facing food-contact areas 108 to provide a textured; linear region on food grabbing surfaces.

FIG. 24 is a perspective view of tongs 110 with truncated cone finger recesses with facing crimp seals 112 which form the food contact areas. While linear regions are shown, it is known that the sealed textured regions can be curved, patterned, crisscrossed or other geometric configuration.

FIG. 25 shows a flat cutout which can be formed to produce tongs 114 with conical finger recesses; two distal rectangular sections 115 connected by strap joint 116, each having a stripe of adhesive at one edge, are formed into the cones and tongs 105 or 107.

FIG. 26 shows tongs 114 made from the plan cutout of FIG. 25.

FIG. 27 shows a coated paper cone 118 and a conical heated mold 120 used to bond the cone 118.

FIG. 28 shows a further alternate embodiment of molded tongs 122 with a shaped or crimped thumb recess 124 and a two-finger recess 125 attached by a strap section 123.

FIG. 29 shows a nested stack 122 of tongs of FIG. 28.

FIG. 30 shows molded tongs 125 with a shaped or crimped thumb recess and a four-finger recess 128 attached by a central strap section 127.

FIG. 31 shows a nested stack 126 of shaped and/or crimped tongs of FIG. 30.

Figure 32:
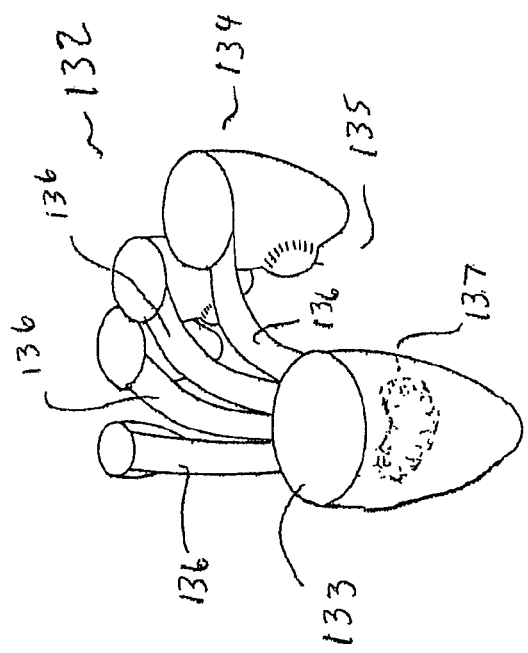
FIG. 32 is a perspective view of yet another embodiment of tongs of this invention comprised of a thumb recess attached to four separate size-appropriate finger recesses each attached to the thumb recess by a separate strap; each of the four finger recesses have protruding food-contact dimples facing the thumb recess which, in turn, has its own elongated protruding dimple (or four separate dimples) facing those of the finger recesses.

FIG. 32 is a perspective view of yet another embodiment of shaped or crimped tongs 132 of this invention comprised of a thumb recess 133 attached to four separate size-appropriate finger recesses 134 each attached to the thumb recess 133 by a separate strap 136; each of the four finger recesses 134 have protruding food-contact dimples 135 facing the thumb recess 133 which, in turn, has its own elongated protruding dimple 137 (or four separate dimples 135 of finger recesses 134) facing those of the finger recesses 134.

Figure 33:
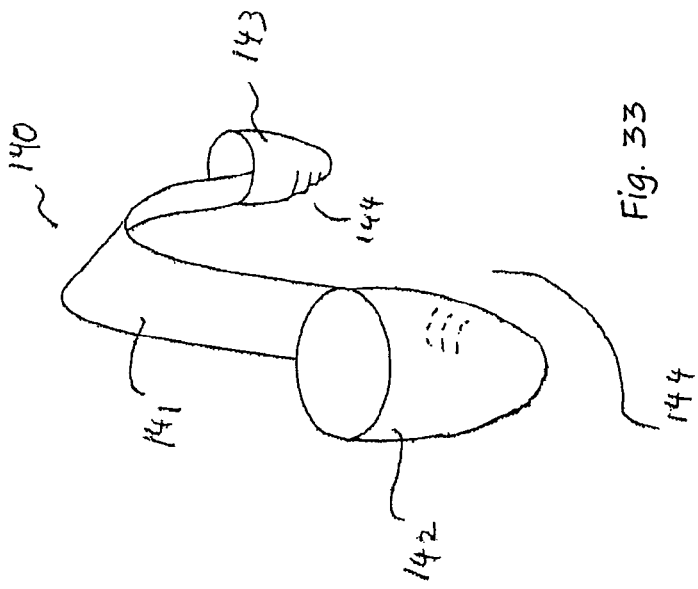
FIG. 33 is a perspective view of tongs with a thumb recess and a smaller finger recess attached by a strap section with facing side food-contact crimped patterns on the two recess sections.

FIG. 33 shows tongs 140 with a thumb recess 142 and a smaller finger recess 143 attached by a strap section 141 with facing side food-contact crimped patterns 144 on the two recess sections.

Figure 34:
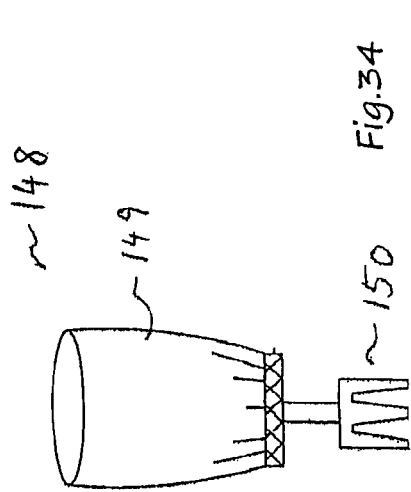
FIG. 34 is perspective view of a food handling accessory with a hand recess attached to a rigid food-contact tool such as the fork illustrated.

FIG. 34 shows an alternate embodiment a food handling accessory 148 with a hand recess 149 attached to a rigid food-contact tool 150 such as the fork illustrated, or other food handling implements, such as knives, spoons or chop sticks.

FIG. 35 shows disposable finger holding tongs for handling a food product including a sheet 160 of disposable flexible coated plastic, plastic or fabric material, or combinations thereof, such as, for example, MYLAR®, or reinforced paper material having a central folded region 161 with opposite foldable distal end wings 162, 163. The distal end wings 162, 163 of the strip 160 form open jaws of the tongs wherein each folded distal end wing 162 and 163 forms a pocket 162a or 163a to accommodate a thumb or at least one finger of a person using the tongs to hold food. A removable seal covers at least the central region of the openings of the disposable finger tongs (or the entire tongs) prior to use. Respective textured surfaces are provided on grabbing surfaces of the jaws to assist in holding the food product; wherein the tongs are formed from the folded sheet 160 of flexible material folded over a set of female dies 164 pressed by a male die 165 to form crimped open three dimensional finger and thumb portions with textured surfaces, such as those shown in FIGS. 28-31 or FIGS. 32 and 33. The folded materials and the complementary dies 164 and 165 are provided under a shroud 166 providing a heat sealing of the tongs.

In the foregoing description, certain terms and visual depictions are used to illustrate the preferred embodiment.

However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention, as noted in the appended Claims.

I claim:

1. Disposable finger holding tongs for handling a food product comprising:
   at least one strip of disposable flexible coated material having a central tab;
   opposite distal ends of said strip forming jaws of said tongs, said tongs having at least one finger stability enhancing method component, each distal end having at least one open finger accommodating region having a first finger insertion hole to accommodate at least one finger or thumb of a user through said first finger insertion hole and into said open finger accommodating region of each jaw of said tongs,
   said stability enhancing method component maintaining at least one finger in said finger accommodating regions for holding said tongs upon the respective fingers and thumb of the user and,
   at least one respective textured surface provided on at least one respective grabbing surface of said jaws of said tongs to assist in holding said food product, wherein said at least one finger stability enhancing method component comprises at least one of the following:
   a) at least one additional finger insertion hole in an area of said at least one strip having said central tab to pass said finger or thumb through said additional finger insertion hole prior to insertion of said finger or thumb through said first finger insertion hole of said open finger accommodating region, said at least one additional finger insertion hole extending completely through both sides of said at least one strip in an area of said at least one strip having said central tab, providing an opening on both respective sides of at least one central tab of said strip, or,
   b) at least one flexible strap in said open finger accommodating region, or,
   c) at least one flexible ring in said open finger accommodating region ,or,
   d) a combination of:
      i) said at least one additional finger insertion hole, and/or
      ii) said at least one flexible strap and/or
      iii) said at least one flexible ring,
   wherein further, said at least one open finger accommodating region comprises at least one of the following:
   e) at least one finger accommodating pocket, or,
   f) at least one flexible strap against which said flexible strap a finger is inserted, or,
   g) at least one strap against which said strap a finger is inserted, or,
   h) a combination of
      iv) said at least one finger accommodating pocket, or,
      v) said at least one flexible strap and/or
      vi) said at least one strap,
   in which said at least one textured surface is provided interchangeable in situ by at least one adhesive sticker;
   wherein said sticker is attached to an elastic or stretchable ring, said elastic or stretchable ring insertable over a respective jaw of said tongs for engaging said sticker to said tong.

2. The disposable finger holding tongs of claim 1 further comprising a removable seal covering at least a central part of said disposable finger tongs connecting both jaws at their respective open mouth portions prior to use to reveal said respective at least one open finger accommodating region being at least one jaw forming an open pocket.

3. The disposable tongs of claim 1 in which at least one of said jaws has an interchangeable food handling utensil tool extending therefrom, said food handling utensil tool selected from the group consisting of a fork, knife, spoon, chopsticks, a meat tearer or a shell cracker.

4. The disposable finger tongs as in claim 1 wherein said stickers include a textured side and an opposite tong engaging side, said opposite tong engaging side having a centralized adhesive region surrounded by a non adhesive peripheral region with free ends not contacting said opposite tong engaging side.

5. The disposable finger holding tongs of claim 1 wherein said at least one finger accommodating regions is a plurality of finger accommodating regions and said at least one stability enhancing method component is a plurality of stability enhancing method components, said plurality of finger accommodating regions and said plurality of stability enhancing method components are located on either side of said disposable finger holding tongs, allowing food grabbing and tasting for use on either side of said finger holding tongs for a plurality of unmixed foods.

6. The disposable finger holding tongs of claim 1 wherein each respective finger accommodating region can accommodate a thumb or at least one finger and vice versa.

7. The disposable finger holding tongs of claim 1 wherein further said central tab of said at least one strip of disposable flexible material is located either in or out of a hand palm contact region of said at least one strip of disposable flexible material, with or without said finger stability method component being said one additional hole in an area of said strip having said central tab.

8. The disposable finger holding tongs of claim 1 wherein further said at least one hole in said area of said strip having said central tab permits respective fingers and thumb of a user to be in or out of said finger accommodating regions comprising a bare fingers and thumb article handling use while said fingers and thumb are still attached to said tongs through said finger stability method component holes in said area of said strip having said central tab region.

9. Disposable finger holding tongs for handling a food product comprising:
   at least one strip of disposable flexible coated material having a central tab;
   opposite distal ends of said strip forming jaws of said tongs, said tongs having at least one finger stability enhancing method component, each distal end having at least one open finger accommodating region having a first finger insertion hole to accommodate at least one finger or thumb of a user through said first finger insertion hole and into said open finger accommodating region of each jaw of said tongs,
   said stability enhancing method component maintaining at least one finger in said finger accommodating regions for holding said tongs upon the respective fingers and thumb of the user and,
   at least one respective textured surface provided on at least one respective grabbing surface of said jaws of said tongs to assist in holding said food product, wherein said at least one finger stability enhancing method component comprises at least one of the following:
   a) at least one additional finger insertion hole in an area of said at least one strip having said central tab to pass said finger or thumb through said additional finger insertion hole prior to insertion of said finger or thumb through said first finger insertion hole of said open finger accommodating region, said at least one additional finger insertion hole extending completely through both sides of said at least one strip in an area of said at least one strip having said central tab, providing an opening on both respective sides of at least one central tab of said strip, or, b) at least one flexible strap in said open finger accommodating region, or, c) at least one flexible ring in said open finger accommodating region, or, d) a combination of:
   i) said at least one additional finger insertion hole and/or
   ii) said at least one flexible strap and/or
   iii) said at least one flexible ring, wherein further, said at least one open finger accommodating region comprises at least one of the following:

e) at least one finger accommodating pocket, or, f) at least one flexible strap against which said flexible strap a finger is inserted, or, g) at least one strap against which said strap a finger is inserted, or, h) a combination of
   iv) said at least one finger accommodating pocket and/or
   v) said at least one flexible strap and/or
   vi) said at least one strap, in which said at least one textured surface is provided interchangeable in situ by at least one adhesive sticker; wherein said at least one sticker further comprises a three-dimensional C-side shaped immovable jaw member having a set of over hanging immovable jaws and ridges on the top and bottom inner surfaces thereof.

10. The disposable finger tongs as in claim 9 further comprising an accessory shell cracker/meat tearer toy removably attachable to said three-dimensional C-side shaped immovable jaw member.

11. The disposable finger holding tongs of claim 9 further comprising a removable seal covering at least a central part of said disposable finger tongs connecting both jaws at their respective open mouth portions prior to use to reveal said respective at least one open finger accommodating region being at least one jaw forming an open pocket.

12. The disposable tongs of claim 9 in which at least one of said jaws has an interchangeable food handling utensil tool extending therefrom, said food handling utensil tool selected from the group consisting of a fork, knife, spoon, chopsticks, a meat tearer or a shell cracker.

13. The disposable finger tongs as in claim 9 wherein said stickers include a textured side and an opposite tong engaging side, said opposite tong engaging side having a centralized adhesive region surrounded by a non adhesive peripheral region with free ends not contacting said opposite tong engaging side. (not needed for claim 20 with crimped texturing)

14. The disposable finger holding tongs of claim 9 wherein said at least one finger accommodating regions is a plurality of finger accommodating regions and said at least one stability enhancing method component is a plurality of stability enhancing method components, said plurality of finger accommodating regions and said plurality of stability enhancing method components are located on either side of said disposable finger holding tongs, allowing food grabbing and tasting for use on either side of said finger holding tongs for a plurality of unmixed foods.

15. The disposable finger holding tongs of claim 9 wherein each respective finger accommodating region can accommodate a thumb or at least one finger and vice versa.

16. The disposable finger holding tongs of claim 9 wherein further said central tab of said at least one strip of disposable flexible material is located either in or out of a hand palm contact region of said at least one strip of disposable flexible material, with or without said finger stability method component being said one additional hole in an area of said strip having said central tab.

17. The disposable finger holding tongs of claim 9 wherein further said central tab of said at least one strip of disposable flexible material is located either in or out of a hand palm contact region of said at least one strip of disposable flexible material, with or without said finger stability method component being said one additional hole in an area of said strip having said central tab.

18. Disposable finger holding tongs for handling a food product comprising:

at least one strip of disposable flexible coated material having a central tab;

opposite distal ends of said strip forming jaws of said tongs, said tongs having at least one finger stability enhancing method component, each distal end having at least one open finger accommodating region having a first finger insertion hole to accommodate at least one finger or thumb of a user through said first finger insertion hole and into said open finger accommodating region of each jaw of said tongs, said stability enhancing method component maintaining at least one finger in said finger accommodating regions for holding said tongs upon the respective fingers and thumb of the user and, at least one respective textured surface provided on at least one respective grabbing surface of said jaws of said tongs to assist in holding said food product, wherein said at least one finger stability enhancing method component comprises at least one of the following:

a) at least one additional finger insertion hole in an area of said at least one strip having said central tab to pass said finger or thumb through said additional finger insertion hole prior to insertion of said finger or thumb through said first finger insertion hole of said open finger accommodating region, said at least one additional finger insertion hole extending completely through both sides of said at least one strip in an area of said at least one strip having said central tab, providing an opening on both respective sides of at least one central tab of said strip, or, b) at least one flexible strap in said open finger accommodating region, or, c) at least one flexible ring in said open finger accommodating region, or, d) a combination of:
   i) said at least, one additional finger insertion hole and/or
   ii) said at least one flexible strap and/or
   iii) said at least one flexible ring, wherein further, said at least one open finger accommodating region comprises at least one of the following:

e) at least one finger accommodating pocket, or, f) at least one flexible strap against which said flexible strap a finger is inserted, or, g) at least one strap against which said strap a finger is inserted, or, h) a combination of
   iv) said at least one finger accommodating pocket and/or
   v) said at least one flexible strap and/or
   vi) said at least one strap, wherein said tongs comprise geometrical members formed from a sheet, said sheet wrapped around to form said geometrical shape, said geometrical members each being provided with respective three dimensional crimped portions forming said textured food grabbing surfaces.

19. The disposable tongs of claim 18 further comprising:
wherein said tongs are formed from at least one folded sheet of flexible material folded over a set of female dies pressed by a set of males dies to form finger stability crimped open three dimensional finger and thumb portions with textured surfaces, said folded materials and said dies being provided under a shroud providing a sealing of said tongs;
wherein one of said tongs has a plurality of finger pockets, each said finger pocket provided for a separate finger of the individual fingers of a user.

20. The disposable finger holding tongs of claim 18 further comprising a removable seal covering at least a central part of said disposable finger tongs connecting both jaws at their respective open mouth portions prior to use to reveal said respective at least one open finger accommodating region being at least one jaw forming an open pocket.

21. The disposable tongs of claim 18 in which at least one of said jaws has an interchangeable food handling utensil tool extending therefrom, said food handling utensil tool selected from the group consisting of a fork, knife, spoon, chopsticks, a meat tearer or a shell cracker.

22. The disposable finger holding tongs of claim 18 wherein said at least one finger accommodating regions is a plurality of finger accommodating regions and said at least one stability enhancing method component is a plurality of stability enhancing method components, said plurality of finger accommodating regions and said plurality of stability enhancing method components are located on either side of said disposable finger holding tongs, allowing food grabbing and tasting for use on either side of said finger holding tongs for a plurality of unmixed foods.

23. The disposable finger holding tongs of claim 18 wherein each respective finger accommodating region can accommodate a thumb or at least one finger and vice versa.

24. The disposable finger holding tongs of claim 18 wherein further said central tab of said at least one strip of disposable flexible material is located either in or out of a hand palm contact region of said at least one strip of disposable flexible material, with or without said finger stability method component being said one additional hole in an area of said strip having said central tab.

25. The disposable finger holding tongs of claim 18 wherein further said central tab of said at least one strip of disposable flexible material is located either in or out of a hand palm contact region of said at least one strip of disposable flexible material, with or without said finger stability method component being said one additional hole in an area of said strip having said central tab.

* * * * *